US011742448B2

(12) United States Patent
Hart et al.

(10) Patent No.: US 11,742,448 B2
(45) Date of Patent: *Aug. 29, 2023

(54) MULTIJUNCTION SOLAR CELLS

(71) Applicant: SolAero Technologies Corp., Albuquerque, NM (US)

(72) Inventors: John Hart, Albuquerque, NM (US); Daniel Derkacs, Albuquerque, NM (US); Zachary Bittner, Albuquerque, NM (US); Andrew Espenlaub, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,162

(22) Filed: Jan. 27, 2022

(65) Prior Publication Data
US 2022/0238741 A1 Jul. 28, 2022

Related U.S. Application Data

(62) Division of application No. 17/574,750, filed on Jan. 13, 2022, and a division of application No. 17/161,314, filed on Jan. 28, 2021, now Pat. No. 11,362,230.

(51) Int. Cl.
*H01L 31/0725* (2012.01)
*H01L 31/0735* (2012.01)
*H01L 31/065* (2012.01)
*H01L 31/18* (2006.01)

(52) U.S. Cl.
CPC ........ *H01L 31/0725* (2013.01); *H01L 31/065* (2013.01); *H01L 31/0735* (2013.01); *H01L 31/184* (2013.01)

(58) Field of Classification Search
CPC ............... H01L 31/065; H01L 31/0687; H01L 31/0693; H01L 31/0725; H01L 31/0735
See application file for complete search history.

(56) References Cited

U.S. PATENT DOCUMENTS

| 6,316,715 | B1 | 11/2001 | King et al. |
| 8,536,445 | B2 | 9/2013 | Cornfeld et al. |
| 8,697,481 | B2 | 4/2014 | Jones-Albertus et al. |

(Continued)

FOREIGN PATENT DOCUMENTS

| CN | 1938866 | 3/2001 |
| CN | 101083290 | 12/2007 |

(Continued)

OTHER PUBLICATIONS

Hwang, et al., Bandgap Grading and Al0.03Ga0.7As Heterojunction Emitter for Highly Efficient GaAs-based Solar Cells, Solar Energy Materials and Solar Cells, Seoul, Korea. 155, pp. 264-272 (2016).

(Continued)

*Primary Examiner* — Golam Mowla

(57) ABSTRACT

A multijunction solar cell including an upper first solar subcell having a first band gap and positioned for receiving an incoming light beam; and a second solar subcell disposed below and adjacent to and lattice matched with said upper first solar subcell, and having a second band gap smaller than said first band gap; wherein at least one of the solar subcells has a graded band gap throughout the thickness of at least a portion of its emitter layer and base layer.

19 Claims, 22 Drawing Sheets

(56) References Cited

U.S. PATENT DOCUMENTS

| | | |
|---|---|---|
| 8,962,993 B2 | 2/2015 | Jones-Albertus et al. |
| 9,666,738 B2 | 5/2017 | Fuhrmann |
| 2003/0070707 A1* | 4/2003 | King .................. H01L 31/02168 136/255 |
| 2003/0145884 A1* | 8/2003 | King .................. H01L 31/0725 136/255 |
| 2004/0065363 A1* | 4/2004 | Fetzer ............... H01L 21/02543 257/E21.112 |
| 2006/0017063 A1 | 1/2006 | Lester |
| 2006/0048811 A1 | 3/2006 | Krut et al. |
| 2006/0144435 A1 | 7/2006 | Wanlass |
| 2007/0193622 A1 | 8/2007 | Sai |
| 2008/0110489 A1 | 5/2008 | Sepehry-Fard |
| 2009/0078309 A1 | 3/2009 | Cornfeld et al. |
| 2010/0006136 A1 | 1/2010 | Zide |
| 2012/0103403 A1* | 5/2012 | Misra ................. H01L 31/0735 438/57 |
| 2013/0048063 A1 | 2/2013 | Walters et al. |
| 2013/0133730 A1 | 5/2013 | Pan et al. |
| 2014/0090700 A1* | 4/2014 | Song .................. H01L 31/0687 438/74 |
| 2014/0182667 A1* | 7/2014 | Richards ............. H01L 31/0725 438/69 |
| 2016/0118526 A1* | 4/2016 | Misra .................. H01L 31/1844 136/255 |
| 2017/0062642 A1* | 3/2017 | Pantha ................ H01L 31/0735 |
| 2017/0110611 A1 | 4/2017 | Cuminal |
| 2017/0133542 A1* | 5/2017 | Derkacs ................ H01L 31/065 |
| 2018/0351020 A1 | 12/2018 | Guter et al. |

FOREIGN PATENT DOCUMENTS

| | | |
|---|---|---|
| CN | 101399298 | 4/2009 |
| CN | 101976689 | 2/2011 |
| EP | 1134813 | 9/2001 |
| EP | 2 779 253 | 9/2014 |
| EP | 3 514 838 | 9/2014 |
| KR | 00787784 | 6/2014 |
| TW | 201327875 | 7/2012 |
| WO | WO 2013107628 | 7/2013 |

OTHER PUBLICATIONS

Hutchby, High-efficiency graded band-gap $Al_xGa_{1-x}As$—GaAs solar cell, Appl. Phys. Lett. 26, 457 (1975); https://doi.org/10.1063/1.88208, Published Online: Sep. 2, 2008 (4 pages).

\* cited by examiner

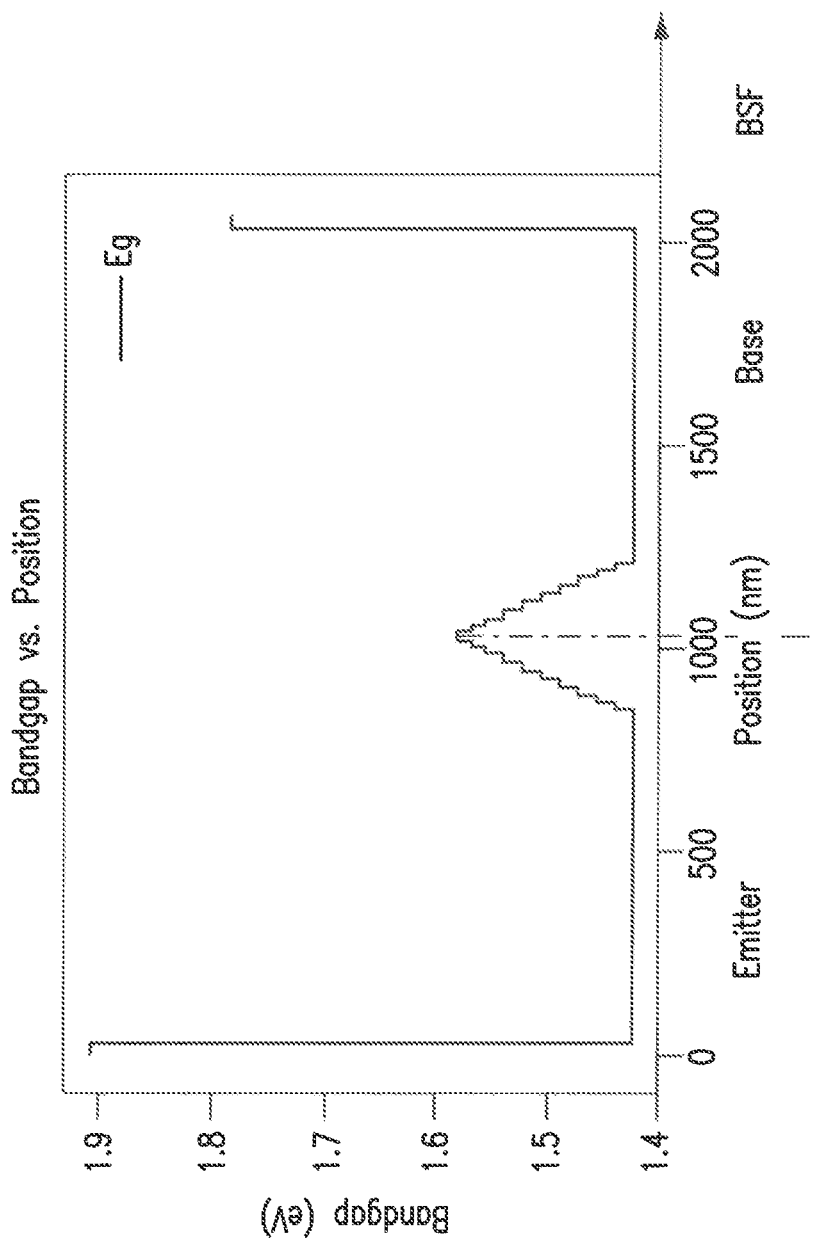

| Cell | Layer | Description | Ref |
|---|---|---|---|
| | n++ GaAs | contact layer | 104 |
| | n+ AlInP$_2$ | window | 105 |
| cell A | n+ AlInGaP$_2$ | n+ emitter | 106 |
| | p AlInGaP$_2$ | p base | 107 |
| | p+ AlGaInP | BSF | 108 |
| | p++ AlGaAs | p++ tunnel diode | 109a |
| | n++ InGaP | n++ tunnel diode | 109b |
| | n+ GaInP$_2$ | window | 110 |
| | | | 111 |
| cell B | n+ GaInP$_2$ or AlGaAs | n+ emitter | 112 |
| | p AlGaAs | p base | |
| | p+ AlGaAs | BSF | 113 |
| | p++ AlGaAs | p++ tunnel diode | 114a |
| | n++ InGaP | n++ tunnel diode | 114b |
| | n+ GaInP | window | 118 |
| cell C | n+ GaAs | n+ emitter | 119 |
| | p GaAs | p base | 120 |
| | p+ GaAlAs | BSF | 121 |
| | | DBR Layers | 122c |
| | p++ GaAs | p+ tunnel diode | 122a |
| | n++ GaAs | n+ tunnel diode | 122b |
| | n GaInP | alpha Layer | 123 |
| | n InGaAlAs | metamorphic buffer layer | 124 |
| | n AlGaInAsP | alpha layer | 125 |
| | n+ InGaAlAs | window | 126 |
| cell D | n+ InGaAs | n+ emitter | 127 |
| | p InGaAs | p base | 128 |
| | p+ InGaAlAs | BSF | 129 |
| | p++ AlGaInAs | p+ tunnel diode | 130a |
| | n+ GaInP | n+ tunnel diode | 130b |
| | n+ GaInP | alpha layer | 131 |
| | n AlGaInAs | metamorphic buffer layer | 132 |
| | n+ GaInP | alpha layer | 133 |
| | n+ GaInP | window | 134 |
| cell E | n+ GaInAs | n+ emitter | 135 |
| | p GaInAs | p base | 136 |
| | p+ AlGaInAs | BSF | 137 |
| | p++ AlGaInAs | p contact layer | 138 |
| | | | 139 |

| Cell | Material | Layer | # |
|---|---|---|---|
| | n++ GaAs | contact layer | 104 |
| | n+ AlInP$_2$ | window | 105 |
| cell A | n+ AlInGaP$_2$ | n+ emitter | 106 |
| | p AlInGaP$_2$ | p base | 107 |
| | p+ AlGaInP$_2$ | BSF | 108 |
| | p++ AlGaAs | p++ tunnel diode | 109a |
| | n++ InGaP | n++ tunnel diode | 109b |
| | n+ GaInP$_2$ | window | 110 |
| cell B | n+ GaInP$_2$ | n+ emitter | 111 |
| | p AlGaAs | p base | 112 |
| | p+ AlGaAs | BSF | 113 |
| | | DBR layers | 114 |
| | p++ AlGaAs | p++ tunnel diode | 114a |
| | n++ InGaP | n++ tunnel diode | 114b |
| | n+ GaInP | window | 118 |
| cell C | n+ GaAs | n+ emitter | 119 |
| | p GaAs | p base | 120 |
| | p+ AlGaAs | BSF | 121 |
| | | DBR Layers | 122c |
| | p++ GaAs | p+ tunnel diode | 122a |
| | n++ GaAs | n+ tunnel diode | 122b |
| | n GaInP | alpha Layer | 123 |
| | n InGaAlAs | metamorphic buffer layer | 124 |
| | n AlGaInAsP | alpha layer | 125 |
| | n+ InGaAlAs | window | 126 |
| cell D | n+ InGaAs | n+ emitter | 127 |
| | p InGaAs | p base | 128 |
| | p+ InGaAlAs | BSF | 129 |
| | p++ AlGaInAs | p+ tunnel diode | 130a |
| | n+ GaInP | n+ tunnel diode | 130b |
| | n+ GaInP | alpha layer | 131 |
| | n AlGaInAs | metamorphic buffer layer | 132 |
| | n+ GaInP | alpha layer | 133 |
| | n+ GaInP | window | 134 |
| cell E | n+ GaInAs | n+ emitter | 135 |
| | p GaInAs | p base | 136 |
| | p+ AlGaInAs | BSF | 137 |
| | p++ AlGaInAs | p contact layer | 138 |
| | | | 139 |

FIG. 6

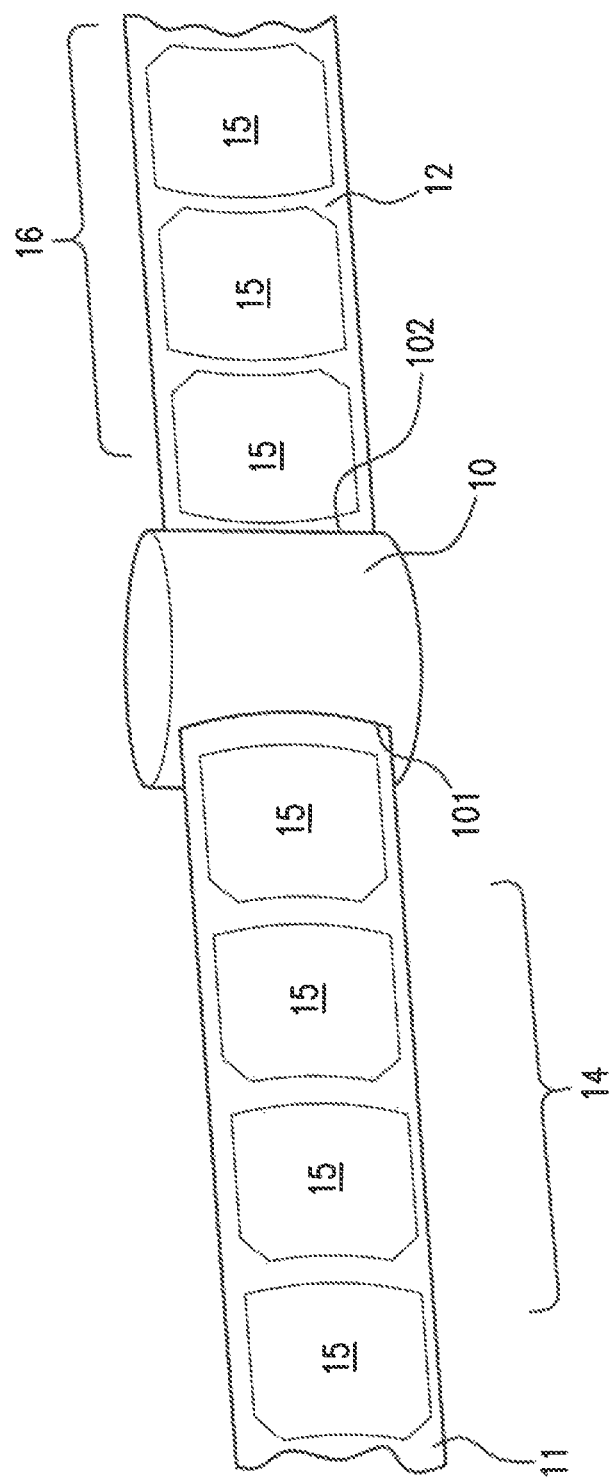

MULTIJUNCTION SOLAR CELLS

REFERENCE TO RELATED APPLICATIONS

The present application is a divisional of U.S. patent application Ser. No. 17/161,314 filed Jan. 28, 2021. U.S. patent application Ser. No. 17/574,750 filed Jan. 13, 2022 is also a divisional of U.S. patent application Ser. No. 17/161,314.

The present application is related to U.S. patent application Ser. No. 15/681,144 filed Aug. 18, 2017, which is a continuation-in-part of Ser. No. 14/828,206 filed Aug. 17, 2015.

This application is related to U.S. patent application Ser. No. 14/660,092 filed Mar. 17, 2015, which is a division of U.S. patent application Ser. No. 12/716,814 filed Mar. 3, 2010, now U.S. Pat. No. 9,018,521; which is a continuation in part of U.S. patent application Ser. No. 12/337,043 filed Dec. 17, 2008.

This application is also related to U.S. patent application Ser. No. 16/667,687 filed. Oct. 29, 2019 which is a division of Ser. No. 13/872,663 filed Apr. 29, 2012, now U.S. Pat. No. 10,541,349, which was also a continuation-in-part of application Ser. No. 12/337,043, filed Dec. 17, 2008.

This application is also related to U.S. patent application Ser. No. 15/873,135 filed Jan. 17, 2018, U.S. patent application Ser. No. 16/504,828 filed Jul. 8, 2019, and patent application Ser. No. 15/203,975 filed Jul. 7, 2016.

This application is also related to U.S. patent application Ser. No. 15/681,144 filed Aug. 18, 2017, now U.S. Pat. No. 10,700,230, and U.S. patent application Ser. No. 16/722,732 filed Dec. 20, 2019.

This application is also related to U.S. patent application Ser. Nos. 14/828,197 and 14/828,206 filed Aug. 17, 2015.

All of the above related applications are incorporated herein by reference in their entirety.

GOVERNMENT RIGHTS STATEMENT

This invention was made with government support under Contracts No. FA 9453 19-C-1001 awarded by the U.S. Air Force. The Government has certain rights in the invention.

BACKGROUND OF THE INVENTION

Field of the Invention

The present disclosure relates to solar cells and the fabrication of solar cells, and more particularly to the design and specification of both lattice matched and lattice mismatched multijunction solar cells adapted for space missions.

DESCRIPTION OF THE RELATED ART

Solar power from photovoltaic cells, also called solar cells, has been predominantly provided by silicon semiconductor technology. In the past several years, however, high-volume manufacturing of III-V compound semiconductor multijunction solar cells for space applications has accelerated the development of such technology. Compared to silicon, III-V compound semiconductor multijunction devices have greater energy conversion efficiencies and generally more radiation resistance, although they tend to be more complex to properly specify and manufacture. Typical commercial III-V compound semiconductor multijunction solar cells have energy efficiencies that exceed 29.5% under one sun, air mass 0 (AM0) illumination, whereas even the most efficient silicon technologies generally reach only about 18% efficiency under comparable conditions. The higher conversion efficiency of III-V compound semiconductor solar cells compared to silicon solar cells is in part based on the ability to achieve spectral splitting of the incident radiation through the use of a plurality of photovoltaic regions with different band gap energies, and accumulating the current from each of the regions.

In satellite and other space related applications, the size, mass and cost of a satellite power system are dependent on the power and energy conversion efficiency of the solar cells used. Putting it another way, the size of the payload and the availability of on-board services are proportional to the amount of power provided. Thus, as payloads use increasing amounts of power as they become more sophisticated, and missions and applications anticipated for five, ten, twenty or more years, the power-to-weight ratio and lifetime efficiency of a solar cell becomes increasingly more important, and there is increasing interest not only the amount of power provided at initial deployment, but over the entire service life of the satellite system, or in terms of a design specification, the amount of power provided at the "end of life" (EOL) which is affected by the radiation exposure of the solar cell over time in a space environment.

Typical III-V compound semiconductor solar cells are fabricated on a semiconductor wafer in vertical, multijunction structures or stacked sequence of solar subcells, each subcell formed with appropriate semiconductor layers and including a p-n photoactive junction. Each subcell is designed to convert photons over different spectral or wavelength bands to electrical current. After the sunlight impinges on the front of the solar cell, and photons pass through the subcells, with each subcell being designed for photons in a specific wavelength band. After passing through a subcell, the photons that are not absorbed and converted to electrical energy propagate to the next subcells, where such photons are intended to be captured and converted to electrical energy.

The individual solar cells or wafers are then disposed in horizontal arrays, with the individual solar cells connected together in an electrical series and/or parallel circuit. The shape and structure of an array, as well as the number of cells it contains, are determined in part by the desired output voltage and current needed by the payload or subcomponents of the payload, the amount of electrical storage capacity (batteries) on the spacecraft, and the power demands of the payloads during different orbital configurations.

A solar cell designed for use in a space vehicle (such as a satellite, space station, or an interplanetary mission vehicle), has a sequence of subcells with compositions and band gaps which have been optimized to achieve maximum energy conversion efficiency for the AM0 solar spectrum in space. The AM0 solar spectrum in space is notably different from the AM1.5 solar spectrum at the surface of the earth, and accordingly terrestrial solar cells are designed with subcell band gaps optimized for the AM1.5 solar spectrum.

There are substantially more rigorous qualification and acceptance testing protocols used in the manufacture of space solar cells to ensure that space solar cells can operate satisfactorily at the wide range of temperatures and temperature cycles encountered in space. These testing protocols include (i) high-temperature thermal vacuum bake-out; (ii) thermal cycling in vacuum (TVAC) or ambient pressure nitrogen atmosphere (APTC); and in some applications (iii) exposure to radiation equivalent to that which would be experienced in the space mission, and measuring the current and voltage produced by the cell and deriving cell performance data.

As used in this disclosure and claims, the term "space-qualified" shall mean that the electronic component (i.e., the solar cell) provides satisfactory operation under the high temperature and thermal cycling test protocols. The exemplary conditions for vacuum bake-out testing include exposure to a temperature of +100° C. to +135° C. (e.g., about +100° C., +110° C., +120° C., +125° C., +135° C.) for 2 hours to 24 hours, 48 hours, 72 hours, or 96 hours; and exemplary conditions for TVAC and/or APTC testing that include cycling between temperature extremes of −180° C. (e.g., about −180° C., −175° C., −170° C., −165° C., −150° C., −140° C., −128° C., 110° C., −100° C., −75° C., or −70° C.) to +145° C. (e.g., about +70° C., +80° C., +90° C., +100° C., +110° C., +120° C., +130° C., +135° C., or +145° C.) for 600 to 32,000 cycles (e.g., about 600, 700, 1500, 2000, 4000, 5000, 7500, 22000, 25000, or 32000 cycles), and in some space missions up to +180° C. See, for example, Fatemi et al., "Qualification and Production of Emcore ZTJ Solar Panels for Space Missions," Photovoltaic Specialists Conference (PVSC), 2013 IEEE 39th (DOI: 10. 1109/PVSC 2013 6745052). Such rigorous testing and qualifications are not generally applicable to terrestrial solar cells and solar cell arrays.

Conventionally, such measurements are made for the AM0 spectrum for "one-sun" illumination, but for PV systems which use optical concentration elements, such measurements may be made under concentrations of 2×, 100×, or 1000× or more.

The space solar cells and arrays experience a variety of complex environments in space missions, including the vastly different illumination levels and temperatures seen during normal earth orbiting missions, as well as even more challenging environments for deep space missions, operating at different distances from the sun, such as at 0.7, 1.0 and 3.0 AU (AU meaning astronomical units). The photovoltaic arrays also endure anomalous events from space environmental conditions, and unforeseen environmental interactions during exploration missions. Hence, electron and proton radiation exposure, collisions with space debris, and/or normal aging in the photovoltaic array and other systems could cause suboptimal operating conditions that degrade the overall power system performance, and may result in failures of one or more solar cells or array strings and consequent loss of power.

A further distinctive difference between space solar cell arrays and terrestrial solar cell arrays is that a space solar cell array utilizes welding and not soldering to provide robust electrical interconnections between the solar cells, while terrestrial solar cell arrays typically utilize solder for electrical interconnections. Welding is required in space solar cell arrays to provide the very robust electrical connections that can withstand the wide temperature ranges and temperature cycles encountered in space such as from 475° C. to +180° C. In contrast, solder joints are typically sufficient to survive the rather narrow temperature ranges (about −40° C. to about +50° C.) encountered with terrestrial solar cell arrays.

A further distinctive difference between space solar cell arrays and terrestrial solar cell arrays is that a space solar cell array utilizes silver-plated metal material for interconnection members, while terrestrial solar cells typically utilize copper wire for interconnects. In some embodiments, the interconnection member can be, for example, a metal plate. Useful metals include, for example, molybdenum; a nickel-cobalt ferrous alloy material designed to be compatible with the thermal expansion characteristics of borosilicate glass such as that available under the trade designation KOVAR from Carpenter Technology Corporation; a nickel iron alloy material having a uniquely low coefficient of thermal expansion available under the trade designation Invar, FeNi36, or 64FeNi; or the like.

An additional distinctive difference between space solar cell arrays and terrestrial solar cell arrays is that space solar cell arrays typically utilize an aluminum honeycomb panel for a substrate or mounting platform. In some embodiments, the aluminum honeycomb panel may include a carbon composite face sheet adjoining the solar cell array. In some embodiments, the face sheet may have a coefficient of thermal expansion (CTE) that substantially matches the CTE of the bottom germanium (Ge) layer of the solar cell that is attached to the face sheet. Substantially matching the CTE of the face sheet with the CTE of the Ge layer of the solar cell can enable the array to withstand the wide temperature ranges encountered in space without the solar cells cracking, delaminating, or experiencing other defects. Such precautions are generally unnecessary in terrestrial applications.

Thus, a further distinctive difference of a space solar cell from a terrestrial solar cell is that the space solar cell must include a cover glass over the semiconductor device to provide radiation resistant shielding from particles in the space environment which could damage the semiconductor material. The cover glass is typically a cerin doped borosilicate glass which is typically from three to six mils in thickness and attached by a transparent adhesive to the solar cell.

In summary, it is evident that the differences in design, materials, and configurations between a space-qualified III-V compound semiconductor solar cell and subassemblies and arrays of such solar cells, on the one hand, and silicon solar cells or other photovoltaic devices used in terrestrial applications, on the other hand, are so substantial that prior teachings associated with silicon or other terrestrial photovoltaic system are simply unsuitable and have no applicability to the design configuration of space-qualified solar cells and arrays. Indeed, the design and configuration of components adapted for terrestrial use with its modest temperature ranges and cycle times often teach away from the highly demanding design requirements for space-qualified solar cells and arrays and their associated components.

The assembly of individual solar cells together with electrical interconnects and the cover glass form a so-called "CIC" (Cell-Interconnected-Cover glass) assembly, which are then typically electrically connected to form an array of series-connected solar cells. The solar cells used in many arrays often have a substantial size; for example, in the case of the single standard substantially "square" solar cell trimmed from a 100 mm wafer with cropped corners, the solar cell can have a side length of seven cm or more.

The radiation hardness of a solar cell is defined as how well the cell performs after exposure to the electron or proton particle radiation which is a characteristic of the space environment. A standard metric is the ratio of the end of life performance (or efficiency) divided by the beginning of life performance (EOL/BOL) of the solar cell. The EOL performance is the cell performance parameter after exposure of that test solar cell to a given fluence of electrons or protons (which may be different for different space missions or orbits). The BOL performance is the performance parameter prior to exposure to the particle radiation.

Charged particles in space could lead to damage to solar cell structures, and in some cases, dangerously high voltage being established across individual devices or conductors in the solar array. These large voltages can lead to catastrophic electrostatic discharging (ESD) events. Traditionally for ESD protection the backside of a solar array may be painted with a conductive coating layer to ground the array to the space plasma, or one may use a honeycomb patterned metal panel which mounts the solar cells and incidentally protects the solar cells from backside radiation.

The radiation hardness of the semiconductor material of the solar cell itself is primarily dependent on a solar cell's minority carrier diffusion length ($L_{min}$) in the base region of the solar cell (the term "base" region referring to the p-type base semiconductor region disposed directly adjacent to an n-type "emitter" semiconductor region, the boundary of which establishes the p-n photovoltaic junction). The less degraded the parameter Linin is after exposure to particle radiation, the less the solar cell performance will be reduced. A number of strategies have been used to either improve $L_{min}$, or make the solar cell less sensitive to $L_{min}$ reductions. Improving $L_{min}$ has largely involved including a gradation in dopant elements in the semiconductor base layer of the subcells so as to create an electric field to direct minority carriers to the junction of the subcell, thereby effectively increasing $L_{min}$. The effectively longer $L_{min}$ will improve the cell performance, even after the particle radiation exposure. Making the cell less sensitive to $L_{min}$ reductions has involved increasing the optical absorption of the base layer such that thinner layers of the base can be used to absorb the same amount of incoming optical radiation.

Another consideration in connection with the manufacture of space solar cell arrays is that conventionally, solar cells have been arranged on a support and interconnected using a substantial amount of manual labor. For example, first individual CICs are produced with each interconnect individually welded to the solar cell, and each cover glass individually mounted. Then, these CICs are connected in series to form strings, generally in a substantially manual manner, including the welding steps from CIC to CIC. Then, these strings are applied to a panel substrate and electrically interconnected in a process that includes the application of adhesive, wiring, etc. All of this has traditionally been carried out in a manual and substantially artisanal manner.

The energy conversion efficiency of multifunction solar cells is affected by such factors as the number of subcells, the thickness of each subcell, the composition and doping of each active layer in a subcell, and the consequential band structure, band gap and electron energy levels, conduction, and absorption of each subcell, as well as the effect of its exposure to radiation in the ambient environment over time. The identification and specification of such design parameters is a non-trivial engineering undertaking, and would vary depending upon the specific space mission and customer design requirements. Since the power output is a function of both the voltage and the current produced by a subcell, a simplistic view may seek to maximize both parameters in a subcell by increasing a constituent element, or the doping level, to achieve that effect. However, in reality, changing a material parameter that increases the voltage may result in a decrease in current, and therefore a lower power output. Such material design parameters are interdependent and interact in complex and often unpredictable ways, and for that reason are not "result effective" variables that those skilled in the art confronted with complex design specifications and practical operational considerations can easily adjust to optimize performance.

Moreover, the current (or more precisely, the short circuit current density $J_{sc}$) and the voltage (or more precisely, the open circuit voltage $V_{oc}$) are not the only factors that determine the power output of a solar cell. In addition to the power being a function of the short circuit density ($J_{sc}$), and the open circuit voltage ($V_{oc}$), the output power is actually computed as the product of $V_{oc}$ and $J_{sc}$, and a Fill Factor (FF). As might be anticipated, the Fill Factor parameter is not a constant, but in fact may vary at a value between 0.5 and somewhat over 0.85 for different arranger tents of elemental compositions, subcell thickness, and the dopant level and profile. Although the various electrical contributions to the Fill Factor such as series resistance, shunt resistance, and ideality (a measure of how closely the semiconductor diode follows the ideal diode equation) may be theoretically understood, from a practical perspective the actual Fill Factor of a given subcell cannot always be predicted, and the effect of making an incremental change in composition or band gap of a layer may have unanticipated consequences and effects on the solar subcell semiconductor material, and therefore an unrecognized or unappreciated effect on the Fill Factor, Stated another way, an attempt to maximize power by varying a composition of a subcell layer to increase the $V_{oc}$ or $J_{sc}$ or both of that subcell, may in fact not result in high power, since although the product $V_{oc}$ and $J_{sc}$ may increase, the FF may decrease and the resulting power also decrease. Thus, the $V_{oc}$ and $J_{sc}$ parameters, either alone or in combination, are not necessarily "result effective" variables that those skilled in the art confronted with complex design specifications and practical operational considerations can easily adjust to optimize performance. Actual experimental evidence of the unpredictability of incrementally modifying a design factor such as composition is illustrated in the discussion of FIG. 7B in this disclosure.

Furthermore, the fact that the short circuit current density ($J_{sc}$), the open circuit voltage ($V_{oc}$), and the fill factor (FF), are affected by the slightest change in such design variables, the purity or quality of the chemical pre-cursors, or the specific process flow and fabrication equipment used, and such considerations further complicates the proper specification of design parameters and predicting the efficiency of a proposed design which may appear "on paper" to be advantageous.

It must be further emphasized that in addition to process and equipment variability, the "fine tuning" of minute changes in the composition, band gaps, thickness, and doping of every layer in the arrangement has critical effect on electrical properties such as the open circuit voltage ($V_{oc}$) and ultimately on the power output and efficiency of the solar cell.

To illustrate the practical effect, consider a design change that results in a small change in the $V_{oc}$ of an active layer in the amount of 0.01 volts, for example changing the $V_{oc}$ from 2.72 to 2:73 volts. Assuming all else is equal and does not change, such a relatively small incremental increase in voltage would typically result in an increase of solar cell efficiency from 29.73% to 29.84% for a triple junction solar cell, which would be regarded as a substantial and significant improvement that would justify implementation of such design change.

For a single junction GaAs subcell in a triple junction device, a change in $V_{oc}$ from 1.00 to 1.01 volts (everything eke being the same) would increase the efficiency of that junction from 10.29% to 10.39%, about a 1% relative increase. If it were a single junction stand-alone solar cell, the efficiency would go from 20.58% to 20.78%, still about a 1% relative improvement in efficiency.

Present day commercial production processes are able to define and establish band gap values of epitaxially deposited layers as precisely as 0.01 eV, so such "fine tuning" of compositions and consequential open circuit voltage results are well within the range of operational production specifications for commercial products.

Another important mechanical or structural consideration in the choice of semiconductor layers for a solar cell is the desirability of the adjacent layers of semiconductor materials in the solar cell, i.e. each layer of crystalline semiconductor material that is deposited and grown to form a solar subcell, have similar or substantially similar crystal lattice constants or parameters.

Here again there are trade-offs between including specific elements in the composition of a layer which may result in improved voltage associated with such subcell and therefore potentially a greater power output, and deviation from exact crystal lattice matching with adjoining layers as a consequence of including such elements in the layer which may result in a higher probability of defects, and therefore lower manufacturing yield.

In that connection, it should be noted that there is no strict definition of what is understood to mean two adjacent layers are "lattice matched" or "lattice mismatched". For purposes in this disclosure, "lattice mismatched" refers to two adjacently disposed materials or layers (with thicknesses of greater than 100 nm) having in-plane lattice constants of the materials in their fully relaxed state differing from one another by less than 0.02% in lattice constant. (Applicant notes that this definition is considerably more stringent than that proposed, for example, in U.S. Pat. No. 8,962,993, which suggests less than 0.6% lattice constant difference as defining "lattice mismatched" layers).

In satellite and other space related applications, the size, mass and cost of a satellite power system are dependent on the power and energy conversion efficiency of the solar cells used. Putting it another way, the size of the payload and the availability of on-board services are proportional to the amount of power provided. Thus, as payloads use increasing amounts of power as they become more sophisticated, and missions and applications anticipated for five, ten, twenty or more years, the power-to-weight ratio and lifetime efficiency of a solar cell becomes increasingly more important, and there is increasing interest not only the amount of power provided at initial deployment, but over the entire service life of the satellite system, or in terms of a design specification, the amount of power provided at the "end of life" (EOL) which is affected by the radiation exposure of the solar cell over time in a space environment.

Typical III-V compound semiconductor solar cells are fabricated on a semiconductor wafer in vertical, multijunction structures or stacked sequence of solar subcells, each subcell formed with appropriate semiconductor layers and including a p-n photoactive junction. Each subcell is designed to convert photons over different spectral or wavelength bands to electrical current. After the sunlight impinges on the front of the solar cell, and photons pass through the subcells, with each subcell being designed for photons in a specific wavelength band. After passing through a subcell, the photons that are not absorbed and converted to electrical energy propagate to the next subcells, where such photons are intended to be captured and converted to electrical energy.

The energy conversion efficiency of multijunction solar cells is affected by such factors as the number of subcells, the thickness of each subcell, the composition and doping of each active layer in a subcell, and the consequential band structure, electron energy levels, conduction, and absorption of each subcell, as well as the effect of its exposure to radiation in the ambient environment over time. The identification and specification of such design parameters is a non-trivial engineering undertaking, and would vary depending upon the specific space mission and customer design requirements. Since the power output is a function of both the voltage and the current produced by a subcell, a simplistic view may seek to maximize both parameters in a subcell by increasing a constituent element, or the doping level, to achieve that effect. However, in reality, changing a material parameter that increases the voltage may result in a decrease in current, and therefore a lower power output. Such material design parameters are interdependent and interact in complex and often unpredictable ways, and for that reason are not "result effective" variables that those skilled in the art confronted with complex design specifications and practical operational considerations can easily adjust to optimize performance. Electrical properties such as the short circuit current density ($J_{sc}$), the open circuit voltage ($V_{oc}$), and the fill factor (FF), which determine the efficiency and power output of the solar cell, are affected by the slightest change in such design variables, and as noted above, to further complicate the calculus, such variables and resulting properties also vary, in a nonuniform manner, over time (i.e. during the operational life of the system) due to exposure to radiation during space missions.

Another important mechanical or structural consideration in the choice of semiconductor layers for a solar cell is the desirability of the adjacent layers of semiconductor materials in the solar cell, i.e. each layer of crystalline semiconductor material that is deposited and gown to form a solar subcell, have similar crystal lattice constants or parameters.

SUMMARY OF THE DISCLOSURE

Objects of the Disclosure

It is an object of the present disclosure to provide increased photoconversion efficiency in a multijunction solar cell for space applications by providing a gradation or increase in band gap in the active region of at least one subcell.

It is another object of the present disclosure to increase the current collection in a subcell of a multijunction solar cell by grading or increasing the band gap in the active layer of at least one subcell from the top surface and/or the bottom surface of the one subcell to the junction of the one subcell.

It is another object of the present disclosure to provide a multijunction solar cell in which the subcell current in at least one subcell is increased per unit area of the subcell to enable a greater amount of power output from the multijunction solar cell by providing a gradation or increase in band gap in the active layer of the at least one subcell in the range of 20 to 300 meV.

It is another object of the present invention to provide a graded band gap in the active layer of a heterojunction solar subcell in a multijunction solar cell so as to improve the radiation performance characteristics at the end-of-life (EOL).

It is another object of the present invention to provide a graded band gap in the active layer in one or more subcells of a multijunction solar cell so as to optimize the solar cell for different radiation environments, such as LEO or GEO satellite orbits.

It is another object of the invention to provide a space vehicle with a solar cell array including solar cells with a graded band gap in the active layer of one or more subcells.

It is another object of the present invention to provide a graded band gap in the active layer so as to increase the and the fill factor (FF) in that subcell compared to a subcell with a constant band gap in the active layer.

It is another object of the present invention to provide a graded band gap in the active layer in at least one subcell in either an upright or inverted metamorphic multijunction solar cell.

Some implementations of the present disclosure may incorporate or implement fewer of the aspects and features noted in the foregoing objects.

Features of the Invention

All ranges of numerical parameters set forth in this disclosure are to be understood to encompass any and all subranges or "intermediate generalizations" subsumed herein. For example, a stated range of "1.0 to 2.0 eV" for a band gap value should be considered to include any and all subranges beginning with a minimum value of 1.0 eV or more and ending with a maximum value of 2.0 eV or less, e.g., 1.1 to 2.0, or 1.3 to 1.4, or 1.5 to 1.9 eV.

Briefly, and in general terms, the present disclosure provides a multijunction solar cell comprising: an upper first solar subcell; a second solar subcell adjacent to said first solar subcell wherein the emitter and base layers of the second solar subcell form a photoelectric junction; a bottom solar subcell disposed under said second solar subcell; wherein the base and emitter layer of at least one of the subcells has a graded band gap throughout at least a portion of the thickness of its active layer with a band gap throughout at least a portion of the thickness of its active layer with a hand gap adjacent the junction in the range of 20 to 300 meV greater than the band gap away from the junction.

In some embodiments the portion which has a graded band gap extends around the junction by a distance between 30% and 200% in length of the length of the diffusion region around the junction.

In some embodiments the band gap of at least one of (i) two or more solar subcells are graded; and (ii) at least one solar subcell is not graded.

In some embodiments, the bottom subcell is composed of germanium and is not graded.

In some embodiments the gradation in the band gap in the semiconductor region of a first conductivity type is different from the graduation in band gap in the semiconductor region of a second conductivity type in the at least one subcell.

In some embodiments, the solar cell is a four junction solar cell with the fourth solar subcell having a band gap in the range of approximately 0.67 eV, the third solar subcell having a band gap in the range of approximately 1.41 eV, the second solar subcell having a band gap in the range of approximately 1.65 to 1.8 eV and the upper first solar subcell having a band gap in the range of 2.0 to 2.15 eV.

In some embodiments the gradation in band gap changes over the thickness of the portion at least one of: (i) linearly; (ii) step-function wise; (iii) quadratically; (iv) exponentially; (v) logarithmically or (vi) other incremental or monotonic function.

In some embodiments the gradation in band gap is symmetric on each side of the junction.

In some embodiments the length of the depletion region is (i) symmetric or non-symmetric around the junction in the at least one solar subcell, and (ii) shorter or longer in the n region than in the p-region, or equal in length in the n and p regions.

In some embodiments the peak band gap is centered approximately Where the Fermi level crosses mid-band.

In some embodiments the maximum graded band gap region is centered on the depletion region.

In some embodiments the upper first solar subcell is composed of indium gallium aluminum phosphide and having a first band gap in the range of 2.0 to 2.2 eV.

In some embodiments these further comprises a second solar subcell disposed adjacent to said first solar subcell wherein the emitter layer of the second solar subcell composed of indium gallium phosphide or aluminum indium gallium arsenide, and a base layer composed of aluminum indium gallium arsenide and forming a photoelectric, junction, and having a second band gap in the range of approximately 1.55 to 1.8 eV and being lattice matched with the upper first solar subcell.

In some embodiments, the band gap is graded in (i) the emitter; (ii) the base; or (iii) both the base and emitter of a solar subcell, and the lattice constant remains the same in the base and in the emitter.

In some embodiments, the change in band gap from the nominal level to the peak is approximately 1.0 eV.

In some embodiments, the band gap decreases from the junction of the one subcell to the bottom surface of the one subcell.

In some embodiments, the change in hand gap is in the range of 20 to 300 meV and peaks at the junction.

In some embodiments, the peak band gap is at a constant band gap plateau centered on the junction.

In some embodiments, the constant band gap plateau is symmetric or non-symmetric around the junction.

In some embodiments, the band gap at the top surface of the at least one solar subcell is equal to the band gap at the bottom surface of the at least one subcell.

In some embodiments, the band gap increases linearly from the top surface of the one subcell to the junction of the one subcell.

In some embodiments, the hand gap decreases linearly from the junction of the one subcell to the bottom surface of the one subcell.

In some embodiments, the band gap is linearly or non-linearly graded in (i) the emitter; (ii) the base; or both the base and the emitter of a sola subcell, or may jump from one band gap level to a higher band gap level in one or more steps.

In some embodiments, such jump in band gap may take place at the junction.

In some embodiments, the solar subcell in which a gradation in band gap is present is a heterojunction.

In some embodiments, the generation of hole-electron pairs is enhanced in certain regions of the active layer due to a change in band gap in regions of the active layer of at least one solar subcell.

In some embodiments, the band gap graded increase from the top surface of the one subcell to the junction of the one subcell results in greater collection at the junction of the one subcell.

In some embodiments, the band gap graded increase from the junction of the one subcell to the bottom surface of the one subcell results in improved current collection in the active layer of the one subcell.

In another aspect, the present disclosure provides a multijunction solar cell comprising: a multijunction solar cell comprising: an upper first solar subcell; a second solar subcell adjacent to said first solar subcell, wherein the emitter and base layers of the second solar subcell form a photoelectric junction; at least a third solar subcell adjacent to said second solar subcell having a third band gap less than that of the second solar subcell and being lattice matched with the second solar subcell; and a bottom solar subcell disposed under said third solar subcell; wherein the base layer of at least one of the first, second, or third subcells has a constant lattice constant and a graded band gap throughout at least a portion of the thickness of its active layer with a higher band gap adjacent the junction, and a lower band gap away from the junction.

In another aspect, the present disclosure provides a multijunction solar cell comprising: an upper first solar subcell; a second solar subcell adjacent to said first solar subcell and including an emitter layer and a base layer and having a second band gap in the range of approximately 1.55 to 1.8 eV and being lattice matched with the upper first solar subcell, wherein the emitter and base layers of the second solar subcell form a photoelectric junction; at least a third solar subcell adjacent to said second solar subcell and having a third band gap less than that of the second solar subcell and being lattice matched with the second solar subcell; wherein at least one of the subcells has a graded band gap throughout at least a portion of the thickness of its active layer.

In another aspect, the present disclosure provides a method of manufacturing a multijunction solar cell comprising the steps of: providing a semiconductor growth substrate; depositing a first sequence of layers of semiconductor material forming first and second solar subcells on the growth substrate; depositing a second sequence of layers of semiconductor material forming at least a lattice matched third solar subcell over the second solar subcell; wherein the base layer of at least one of the second or third solar subcells has a graded band gap throughout at least a portion of the thickness of its active layer with the semiconductor material having a lower band gap adjacent the junction, and a higher band gap away from the junction in the range of 20 to 300 meV greater than the lower band gap, and a constant lattice constant throughout its thickness; and removing the growth substrate so that the first solar subcell forms the top or light-facing subcell of the multijunction solar cell.

In another aspect, the present disclosure provides a method of manufacturing a multijunction solar cell comprising: providing a semiconductor growth substrate forming a bottom subcell; depositing a first sequence of layers of semiconductor material forming first and second solar subcells on the growth substrate; depositing a second sequence of layers of semiconductor material forming at least a third solar subcell over and lattice matched to the second solar subcell; wherein the base layer of at least one of the second or third solar subcells has a graded band gap throughout at least a portion of the thickness of its active layer with the semiconductor material having a lower band gap adjacent the junction, and a higher band gap away from the junction in the range of 20 to 300 eV greater than the lower band gap, and a constant lattice constant throughout its thickness.

In some embodiments, the solar cell is an upright or four junction solar cell with the first, second, or third junctions having a graded band gap.

Another descriptive aspect of the present disclosure is to characterize the fourth subcell as having a direct band gap of greater than 0.75 eV. The indirect band gap of germanium at room temperature is about 0.66 eV, while the direct band gap of germanium at room temperature is 0.8 eV. Those skilled in the art will normally refer to the "band gap" of germanium as 0.66 eV, since it is lower than the direct band gap value of 0.8 eV.

The recitation that "the fourth subcell has a direct band gap of greater than 0.75 eV" is therefore expressly meant to include germanium as a possible semiconductor for the fourth subcell, although other semiconductor material can be used as well.

In some embodiments, the solar cell is an upright five junction solar cell with the first, second, or third junctions having a graded band gap.

In some embodiments, the solar cell is an upright three junction solar cell with the first and/or second junction having a graded band gap.

In some embodiments, the solar cell is an inverted two junction solar cell with the first and/or second junction having a graded band gap.

In some embodiments, the solar cell is an inverted three junction solar cell with the first, second and/or third junction having a graded band gap.

In some embodiments, the solar cell is an inverted four junction solar cell with the first, second, third, and/or fourth junction having a graded band gap.

In some embodiments, the solar cell is an inverted five junction solar cell with the first, second, third, fourth and/or fifth junction having a graded band gap.

In some embodiments, the solar cell is an inverted six junction solar cell with the first, second, third, fourth, fifth and/or sixth junction having a graded band gap.

In some embodiments, additional layer(s) may be added or deleted in the cell structure without departing from the scope of the present disclosure.

Some implementations of the present disclosure may incorporate or implement fewer of the aspects and features noted in the foregoing summaries.

Additional aspects, advantages, and novel features of the present disclosure will become apparent to those skilled in the art from this disclosure, including the following detailed description as well as by practice of the disclosure. While the disclosure is described below with reference to preferred embodiments, it should be understood that the disclosure is not limited thereto. Those of ordinary skill in the art having access to the teachings herein will recognize additional applications, modifications and embodiments in other fields, which are within the scope of the disclosure as disclosed and claimed herein and with respect to which the disclosure could be of utility.

BRIEF DESCRIPTION OF THE DRAWINGS

The present disclosure will be better and more fully appreciated by reference to the following detailed description when considered in conjunction with the accompanying drawings, wherein:

FIG. 1G is a graph illustrating the band gap versus depth of a solar subcell with one example of an increasing graded band gap in a single junction test solar subcell with a band gap of approximately 1.42 eV;

FIG. 5B is a cross-sectional view of the solar cell of FIG. 5A after removal of the growth substrate, and with the first-grown subcell A depicted at the top of the Figure;

FIG. 6 is a cross-sectional view of a sixth embodiment of a solar cell after several stages of fabrication including the growth of certain semiconductor layers and removal of the growth substrate, according to the present disclosure;

FIG. 9 is a highly simplified perspective illustration of an exemplary space vehicle including a deployable flexible sheet including an array of solar cells according to the present disclosure.

GLOSSARY OF TERMS

Figure 1A:
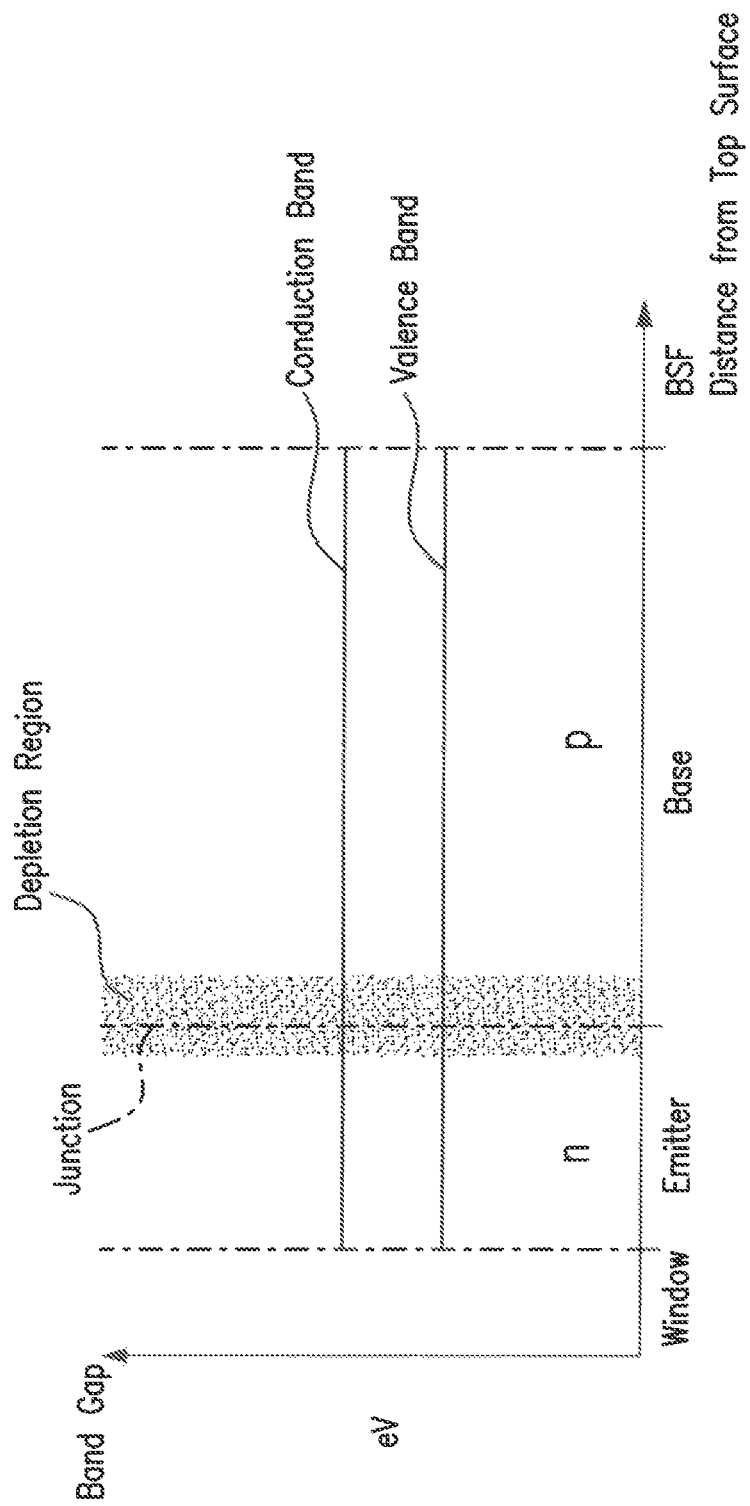
FIG. 1A is a graph of the band gap throughout the thickness of a solar subcell in a multijunction solar cell according to the prior art.

"III-V compound semiconductor" refers to a compound semiconductor formed using at least one element from group III of the periodic table and at least one element from group V of the periodic table. III-V compound semiconductors include binary, tertiary and quaternary compounds. Group III includes boron (B), aluminum (Al), gallium (Ga), indium (In) and thallium (T). Group V includes nitrogen (N), phosphorus (P), arsenic (As), antimony (Sb) and bismuth (Bi).

"Band gap" refers to an energy difference (e.g., in electron volts (eV)) separating the top of the valence hand and the bottom of the conduction band of a semiconductor material.

"Beginning of Life (BOL)" refers to the time at which a photovoltaic power system is initially deployed in operation.

"Bottom subcell" refers to the subcell in a multifunction solar cell which is furthest from the primary light source for the solar cell.

"Compound semiconductor" refers to a semiconductor formed using two or more chemical elements.

"Current density" refers to the short circuit current density $J_s$ through a solar subcell through a given planar area, or volume, of semiconductor material constituting the solar subcell.

"Deposited", with respect to a layer of semiconductor material, refers to a layer of material which is epitaxially gown over another semiconductor layer.

"End of Life (EOL)" refers to a predetermined time or times after the Beginning of Lite, during which the photovoltaic power system has been deployed and has been operational. The EOL time or times may, for example, be specified by the customer as part of the required technical performance specifications of the photovoltaic power system to allow the solar cell designer to define the solar cell subcells and sublayer compositions of the solar cell to meet the technical performance requirement at the specified time or times, in addition to other design objectives. The terminology "EOL" is not meant to suggest that the photovoltaic power system is not operational or does not produce power after the EOL time.

"Graded interlayer" (or "grading interlayer")—see "metamorphic layer".

"Inverted metamorphic multifunction solar cell" or "IMM solar cell" refers to a solar cell in which the subcells are deposited or grown on a substrate in a "reverse" sequence such that the higher band gap subcells, which would normally be the "top" subcells facing the solar radiation in the final deployment configuration, are deposited or grown on a growth substrate prior to depositing or growing the lower band gap subcells.

"Layer" refers to a relatively planar sheet or thickness of semiconductor or other material. The layer may be deposited or grown, by epitaxial or other techniques.

"Metamorphic layer" or "graded interlayer" refers to a layer that achieves a gradual transition in lattice constant generally throughout its thickness in a semiconductor structure.

"Middle subcell" refers to a subcell in a multifunction solar cell which is neither a Top Subcell (as defined herein) nor a Bottom Subcell (as defined herein).

"Short circuit current ($I_{sc}$)" refers to the amount of electrical current through a solar cell or solar subcell when the voltage across the solar cell is zero volts, as represented and measured, for example, in units of milliamps.

"Short circuit current density"—see "current density".

"Solar cell" refers to an electronic device operable to convert the energy of light directly into electricity by the photovoltaic effect.

"Solar cell assembly" refers to two or more solar cell subassemblies interconnected electrically with one another.

"Solar cell subassembly" refers to a stacked sequence of layers including one or more solar subcells.

"Solar subcell" refers to a stacked sequence of layers including a p-n photoactive junction composed of semiconductor materials. A solar subcell is designed to convert photons over different spectral or wavelength bands to electrical current.

"Substantially current matched" refers to the short circuit current through adjacent solar subcells being substantially identical (i.e. within plus or minus 1%).

"Top subcell" or "upper subcell" refers to the subcell in a multijunction solar cell which is closest to the primary light source for the solar cell.

"ZTJ" refers to the product designation of a commercially available SolAero Technologies Corp. triple junction solar cell.

DESCRIPTION OF THE PREFERRED EMBODIMENT

Details of the present invention will now be described including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of the actual embodiment nor the relative dimensions of the depicted elements, and are not drawn to scale.

A variety of different features of multijunction solar cells (as well as inverted metamorphic multijunction solar cells) are disclosed in the related applications noted above. Some, many or all of such features may be included in the structures and processes associated with the inverted multijunction solar cells of the present disclosure.

Prior to discussing the specific embodiments of the present disclosure, a brief discussion of some of the issues associated with the design of multijunction solar cells, and the context of the composition or deposition of various specific layers in embodiments of the product as specified and defined by Applicant is in order.

There are a multitude of properties that should be considered in specifying and selecting the composition of, inter alia, a specific semiconductor layer, the back metal layer, the adhesive or bonding material, or the composition of the supporting material for mounting a solar cell thereon. For example, some of the properties that should be considered when selecting a particular layer or material are electrical properties (e.g., conductivity), optical properties (e.g., band gap, absorbance and reflectance), structural properties (e.g., thickness, strength, flexibility, Young's modulus, etc.), chemical properties (e.g., growth rates, the "sticking coefficient" or ability of one layer to adhere to another, stability of dopants and constituent materials with respect to adjacent layers and subsequent processes, etc.), thermal properties (e.g., thermal stability under temperature changes, coefficient of thermal expansion), and manufacturability (e.g., availability of materials, process complexity, process variability and tolerances, reproducibility of results over high volume, reliability and quality control issues).

In view of the trade-offs among these properties, it is not always evident that the selection of a material based on one of its characteristic properties is always or typically "the best" or "optimum" from a commercial standpoint or for Applicant's purposes. For example, theoretical studies may suggest the use of a quaternary material with a certain band gap for a particular subcell would be the optimum choice for that subcell layer based on fundamental semiconductor physics. As an example, the teachings of academic papers and related proposals for the design of very high efficiency (over 40%) solar cells may therefore suggest that a solar cell designer specify the use of a quaternary material (e.g., InGaAsP) for the active layer of a subcell. A few such devices may actually be fabricated by other researchers, efficiency measurements made, and the results published as an example of the ability of such researchers to advance the progress of science by increasing the demonstrated efficiency of a compound semiconductor multi junction solar cell. Although such experiments and publications are of "academic" interest, from the practical perspective of the Applicants in designing a compound semiconductor multijunction solar cell to be produced in high volume at reasonable cost and subject to manufacturing tolerances and variability inherent in the production processes, such an "optimum" design from an academic perspective is not necessarily the most desirable design in practice, and the teachings of such studies more likely than not point in the wrong direction and lead away from the proper design direction. Stated another way, such references may actually "teach away" from Applicant's research efforts and direction and the ultimate solar cell design proposed by the Applicants.

In view of the foregoing, it is further evident that the identification of one particular constituent element (e.g. indium, or aluminum) in a particular subcell, or the thickness, band gap, doping, or other characteristic of the incorporation of that material in a particular subcell, is not a single "result effective variable" that one skilled in the art can simply specify and incrementally adjust to a particular level and thereby increase the power output and efficiency of a solar cell.

Even when it is known that particular variables have an impact on electrical, optical, chemical, thermal or other characteristics, the nature of the impact often cannot be predicted with much accuracy, particularly when the variables interact in complex ways, leading to unexpected results and unintended consequences. Thus, significant trial and error, which may include the fabrication and evaluative testing of many prototype devices, often over a period of time of months if not years, is required to determine whether a proposed structure with layers of particular compositions, actually will operate as intended, let alone whether it can be fabricated in a reproducible high volume manner within the manufacturing tolerances and variability inherent in the production process, and necessary for the design of a commercially viable device.

Furthermore, as in the case here, where multiple variables interact in unpredictable ways, the proper choice of the combination of variables can produce new and unexpected results, and constitute an "inventive step".

The efficiency of a solar cell is not a simple linear algebraic equation as a function of the amount of gallium or aluminum or other element in a particular layer. The growth of each of the epitaxial layers of a solar cell in a reactor is a non-equilibrium thermodynamic process with dynamically changing spatial and temporal boundary conditions that is not readily or predictably modeled. The formulation and solution of the relevant simultaneous partial differential equations covering such processes are not within the ambit of those of ordinary skill in the art in the field of solar cell design.

More specifically, the present disclosure intends to provide a relatively simple and reproducible technique that is suitable for use in a high volume production environment in which various semiconductor layers are grown on a growth substrate in an MOCVD reactor, and subsequent processing steps are defined and selected to minimize any physical damage to the quality of the deposited layers, thereby ensuring a relatively high yield of operable solar cells meeting specifications at the conclusion of the fabrication processes.

The lattice constants and electrical properties of the layers in the semiconductor structure are preferably controlled by specification of appropriate reactor growth temperatures and times, and by use of appropriate chemical composition and dopants. The use of a deposition method, such as Molecular Beam Epitaxy (MBE), Organo Metallic Vapor Phase Epitaxy (OMVPE), Metal Organic Chemical Vapor Deposition (MOCVD), or other vapor deposition methods for the growth may enable the layers in the monolithic semiconductor structure forming the cell to be grown with the required thickness, elemental composition, dopant concentration and grading and conductivity type, and are within the scope of the present disclosure.

The present disclosure is in one embodiment directed to a growth process using a metal organic chemical vapor deposition (MOCVD) process in a standard, commercially available reactor suitable for high volume production. Other embodiments may use other growth technique, such as MBE. More particularly, regardless of the growth technique, the present disclosure is directed to the materials and fabrication steps that are particularly suitable for producing commercially viable multi junction solar cells or inverted metamorphic multijunction solar cells using commercially available equipment and established high-volume fabrication processes, as contrasted with merely academic expositions of laboratory or experimental results.

Some comments about MOCVD processes used in one embodiment are in order here.

It should be noted that the layers of a certain target composition in a semiconductor structure grown in an MOCVD process are inherently physically different than the layers of an identical target composition gown by another process, e.g. Molecular Beam Epitaxy (MBE). The material quality (i.e., morphology, stoichiometry, number and location of lattice traps, impurities, and other lattice defects) of an epitaxial layer in a semiconductor structure is different depending upon the process used to grow the layer, as well as the process parameters associated with the growth. MOCVD is inherently a chemical reaction process, while MBE is a physical deposition process. The chemicals used in the MOCVD process are present in the MOCVD reactor and interact with the wafers in the reactor, and affect the composition, doping, and other physical, optical and electrical characteristics of the material. For example, the precursor gases used in an MOCVD reactor (e.g. hydrogen) are incorporated into the resulting processed wafer material, and have certain identifiable electro-optical consequences which are more advantageous in certain specific applications of the semiconductor structure, such as in photoelectric conversion in structures designed as solar cells. Such high order effects of processing technology do result in relatively minute but actually observable differences in the material quality grown or deposited according to one process technique compared to another. Thus, devices fabricated at least in part using an MOCVD reactor or using a MOCVD process have inherent different physical material characteristics, which may have an advantageous effect over the identical target material deposited using alternative processes.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIG. 1A is a graph of the band gap throughout the thickness of a solar subcell, depicting the emitter and base regions, the junction, the depletion region around the junction, and the conduction and valence bands defining a certain constant band gap. In this embodiment of the present disclosure, the depletion region is not symmetric around the junction.

Figure 1B:
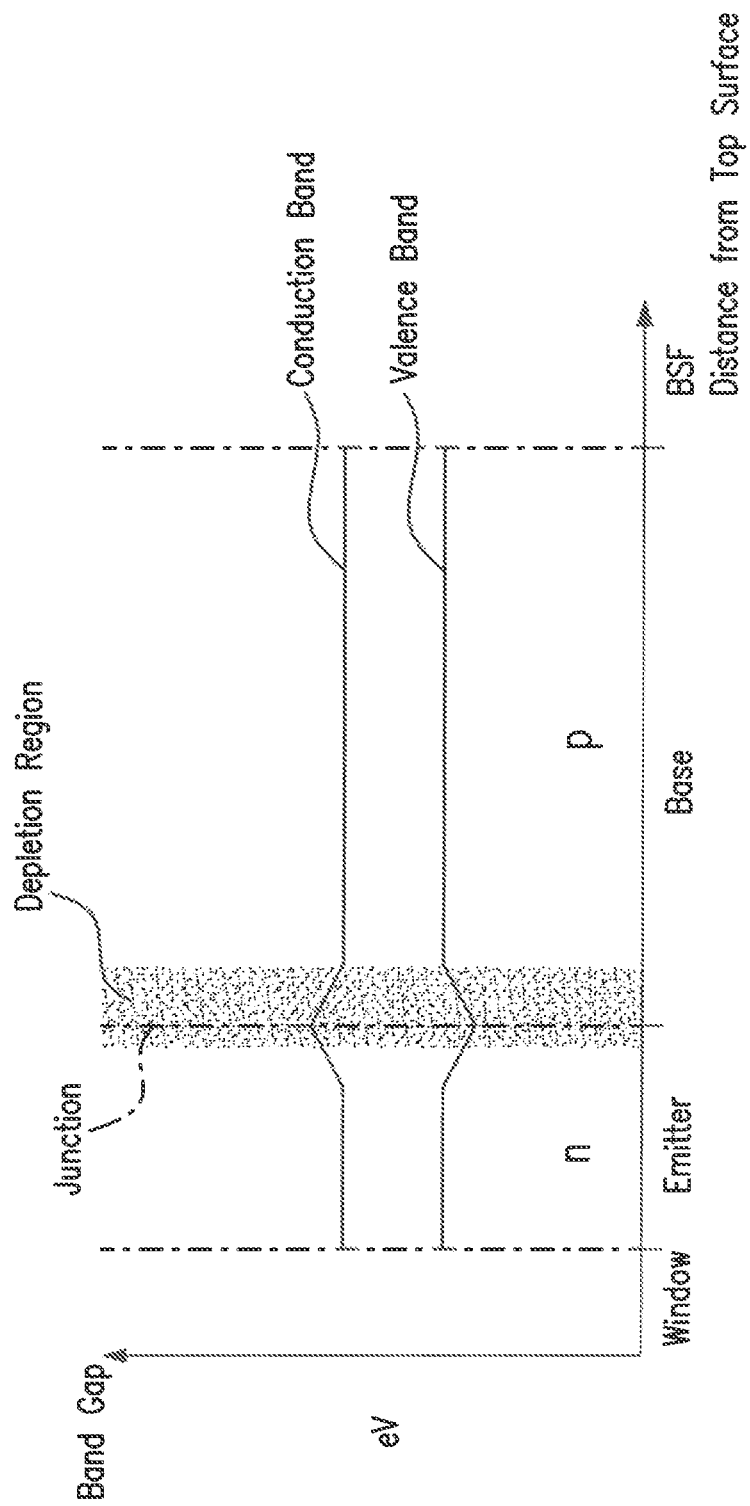
FIG. 1B is a graph of the band gap throughout the thickness of a solar subcell in a multijunction solar cell according to a first embodiment of the present disclosure.

FIG. 1B is a cross-sectional view and graph of the band gap throughout the thickness of a solar subcell in a multijunction solar cell according to an embodiment of the present disclosure, in which the band gap is graded both in the emitter and base regions, and in which in the emitter region the band gap increases from the nominal band gap such as shown in FIG. 1A to a maximum value at the junction, and then decreases in the base region back down to the nominal band gap.

Figure 1C:
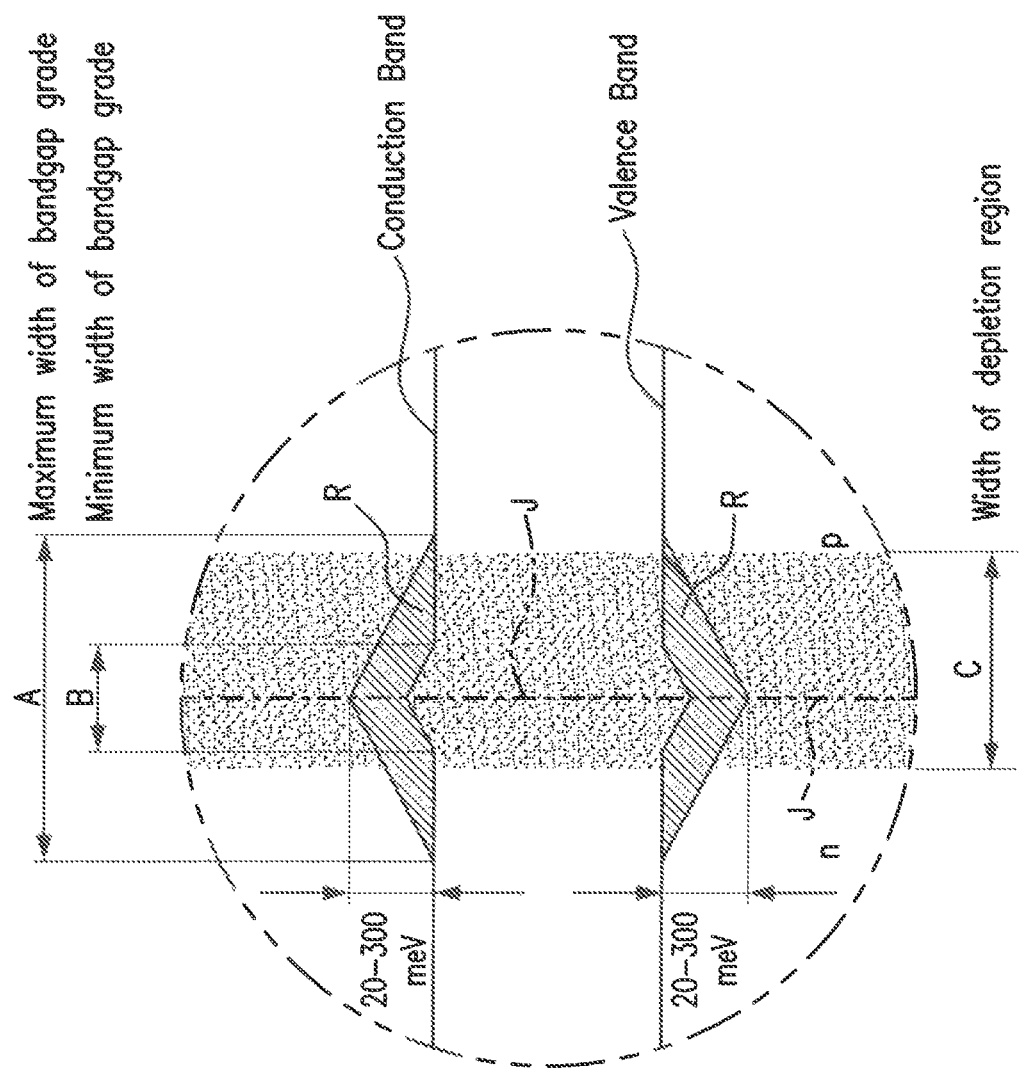
FIG. 1C is an enlarged view of the graph of the band gap depletion region around the junction of the solar subcell of FIG. 1B depicting a range in the regions in which a graded band gap may be implemented.

FIG. 1C is an enlarged view of the depletion region around the junction of the solar subcell of FIG. 1B showing a range of band gaps around the junction J in which the gradation in band gap may be implemented anywhere in the hatched region R.

Figure 1D:
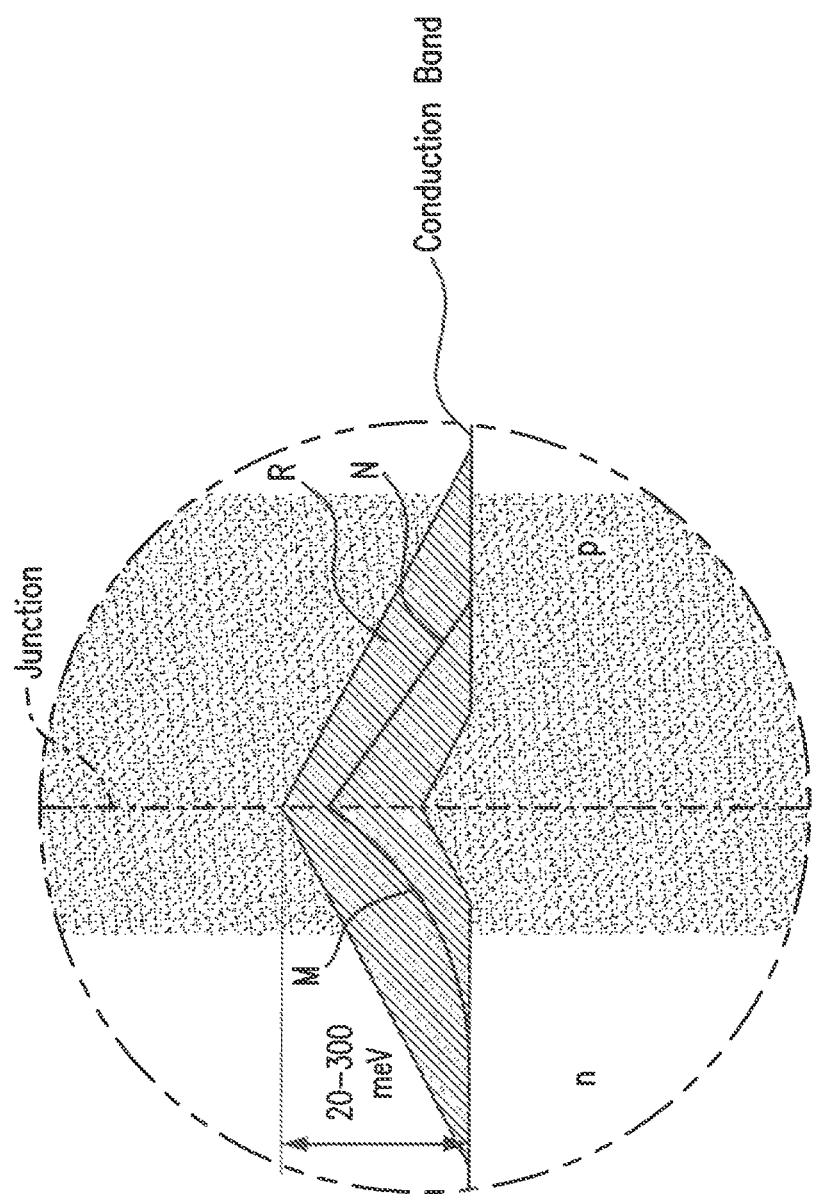
FIG. 1D is a still further enlarged view of the graph of the band gap around the depletion region of FIG. 1C depicting two specific examples of a graded band gap.

FIG. 1D is a still further enlarged view of the depletion region of FIG. 1C depicting the region just the conduction band and depicting examples M and N of two different types of gradation of the band gap, one (M) being exponential, and the other (N) being linear.

Figure 1E:
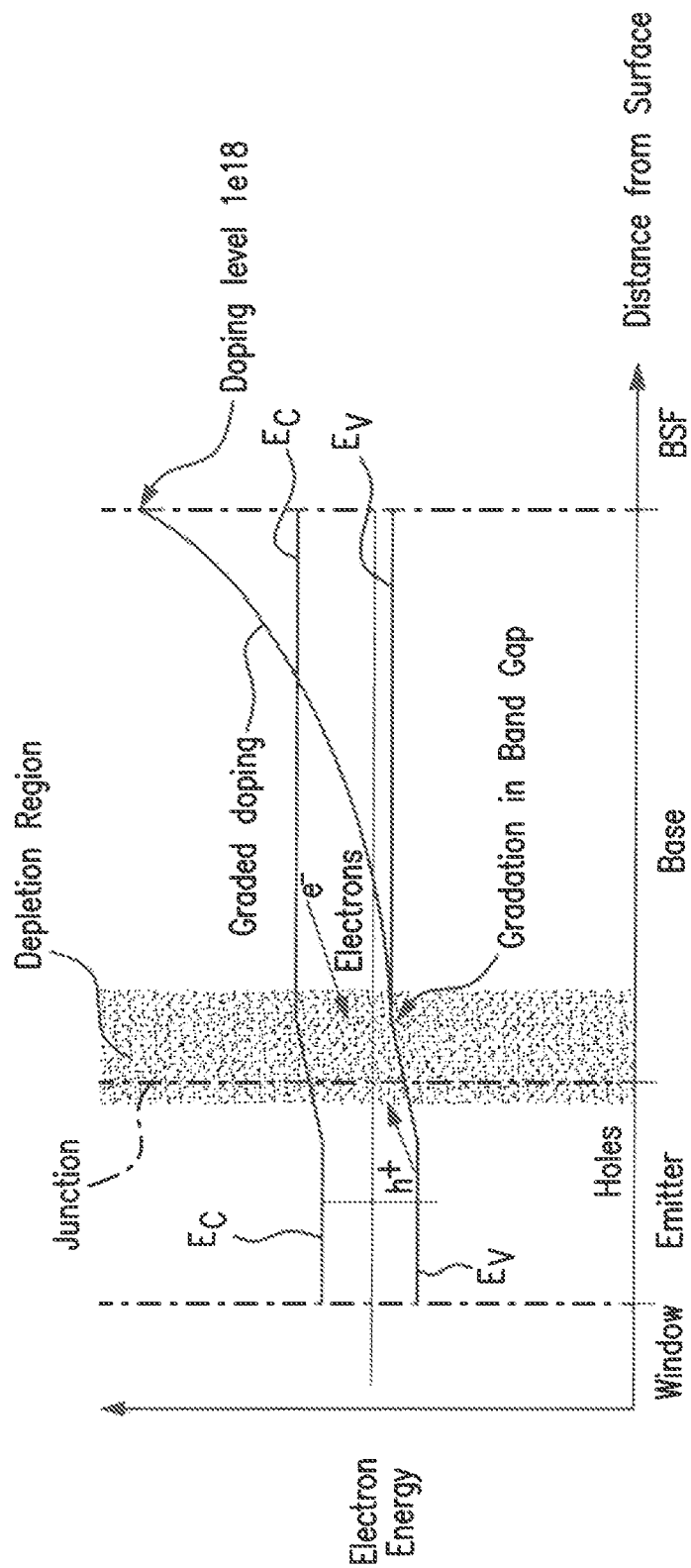
FIG. 1E is a band diagram of the solar subcell of FIG. 1B depicting the movement of electrons and holes throughout the thickness of the layer due to the internal electric field produced by the graded doping in the first embodiment.

FIG. 1E is a band diagram of the solar subcell of FIG. 1B now including the doping present in the emitter and base regions (described in connection with FIG. 2 et al) and depicting the movement of electrons and holes throughout the thickness of the layer due to the internal electric field. The conduction band $E_c$ and the valence band $E_v$ are illustrated, as well as the emitter and base regions of the solar subcell, the junction, the depletion region, and graded doping throughout the thickness of the subcell.

Figure 1F:
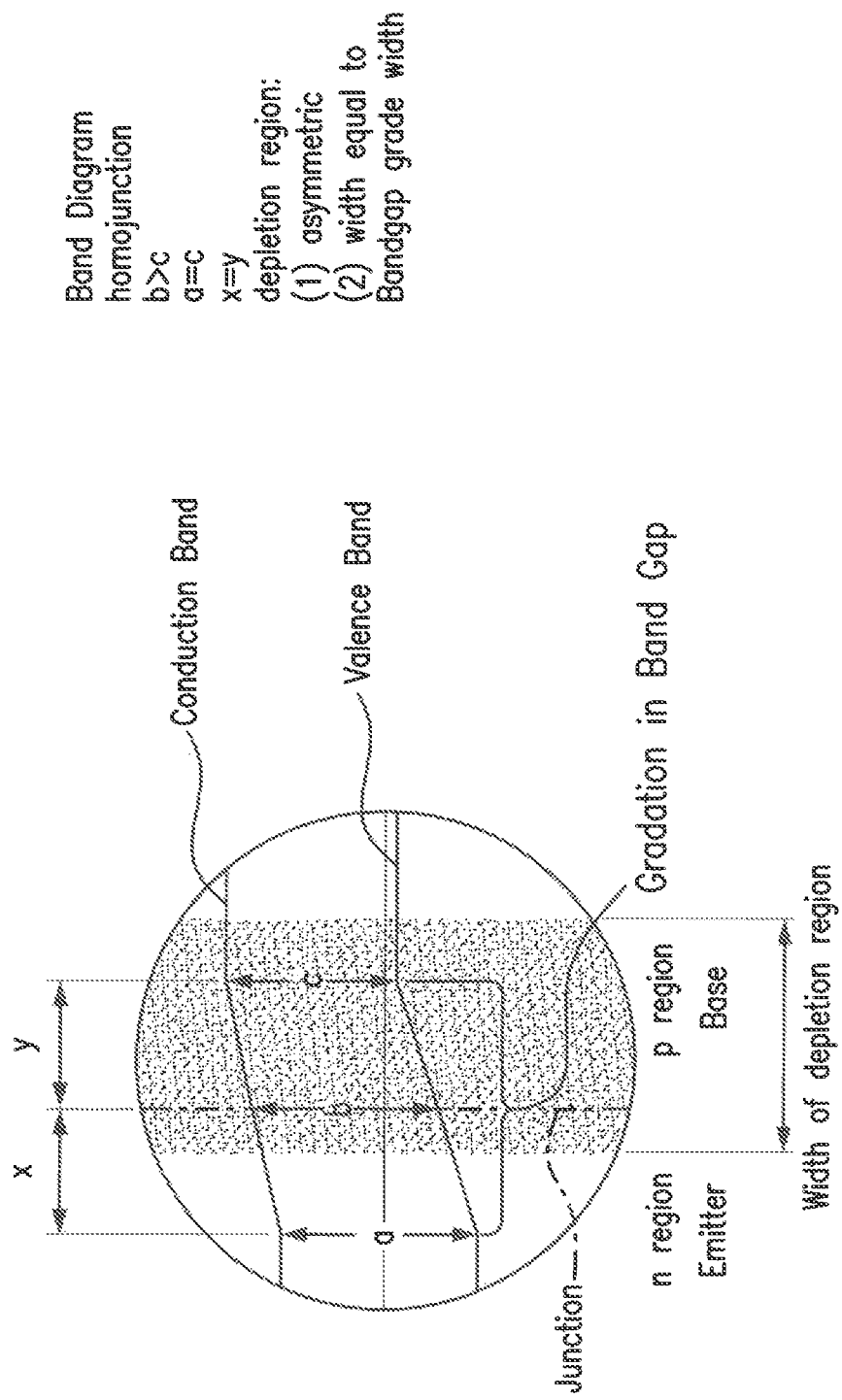
FIG. 1F is an enlarged cross-sectional view of the band diagram of FIG. 1E in the region around the junction.

FIG. 1F is an enlarged cross-sectional view of the band diagram of FIG. 1E in the region around the junction.

FIG. 1G is a graph illustrating the band gap versus position of a solar subcell with a step-wise increasing graded band gap in a solar subcell with a nominal band gap of approximately 1.42 eV.

Figure 1H:
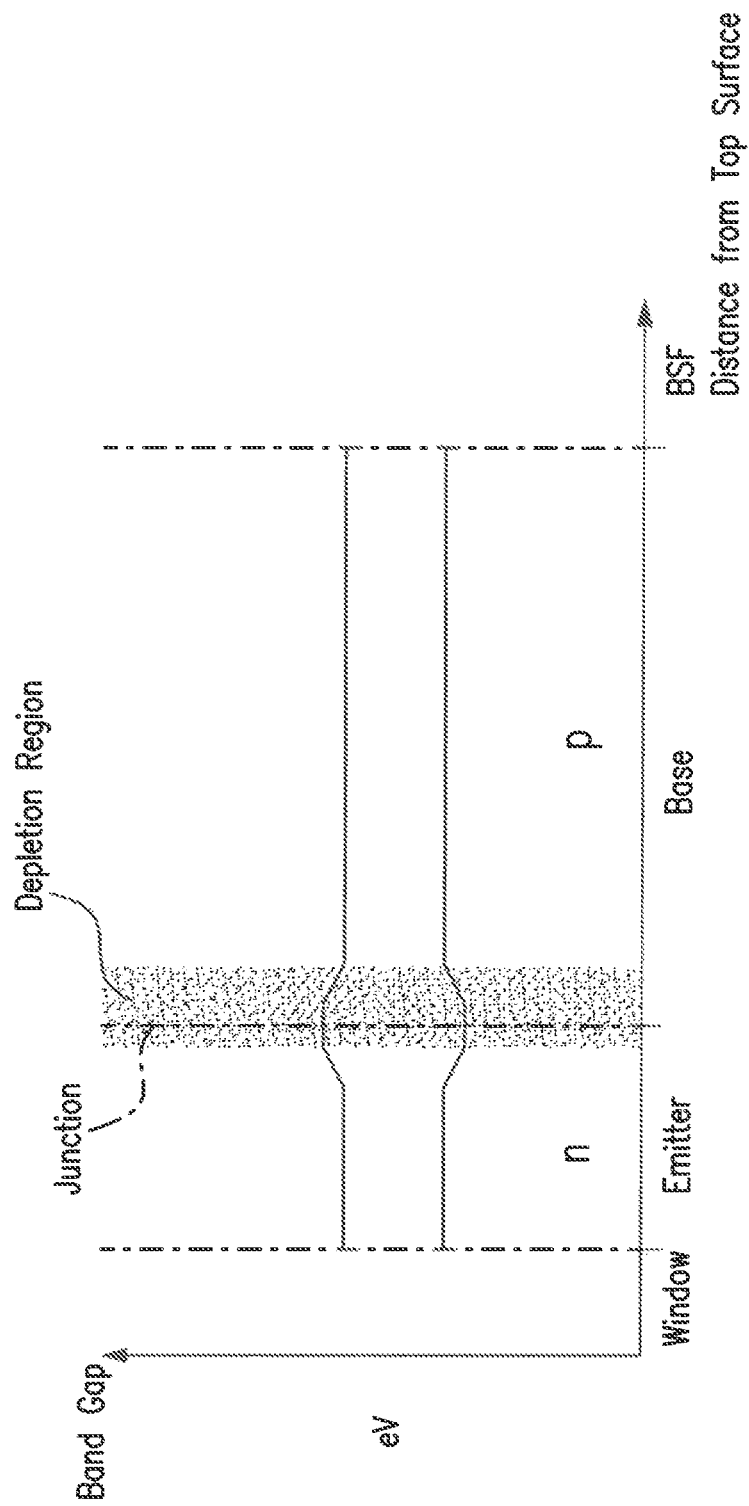
FIG. 1H is a graph illustrating the band gap throughout the thickness of a solar subcell similar to that of FIG. 1B in a multijunction solar cell according to a second embodiment of the present disclosure.

FIG. 1H is a and graph illustrating the band gap throughout the thickness of a solar subcell similar to that of FIG. 1B in a multijunction solar cell according to a second embodiment of the present disclosure, in which the band gap is graded both in the emitter and base regions, in Which in the emitter region it increases from the nominal band gap such as shown in FIG. 1A to a plateau at a higher band gap around the junction, and then decreases in the base region back down to the nominal band gap.

In some embodiments, the gradation in band gap increases to a certain level that is 20 meV to 300 meV greater than the nominal level, and then remains constant and plateaus at that level in the emitter region and continues at that level into the base regions symmetrically (or in other embodiments, non-symmetrically) around the junction. The gradation in band gap then decreases in the base region to the nominal band gap level as depicted in FIG. 1H.

Figure 2A:
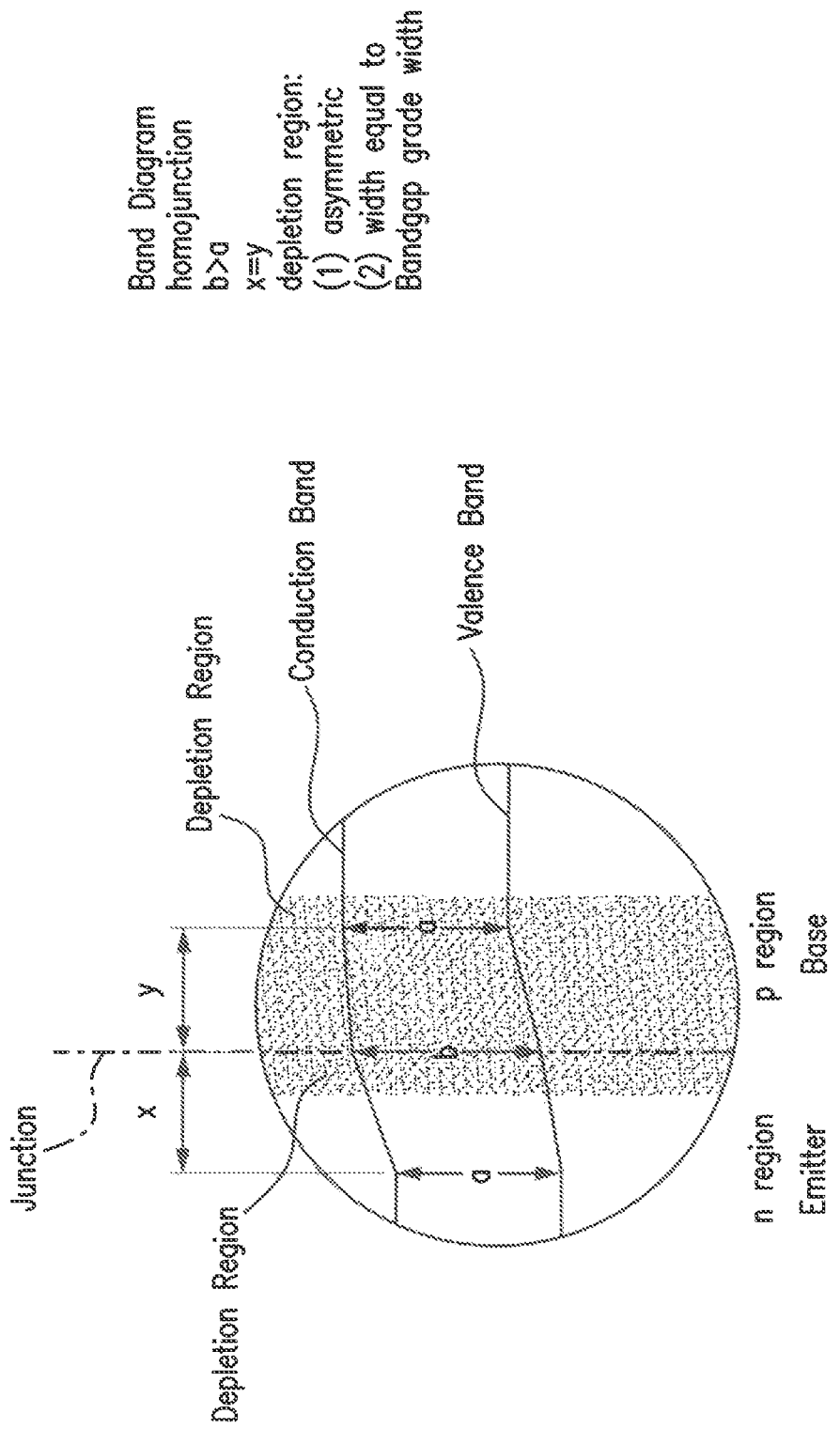
FIG. 2A is an enlarged view of the band diagram around the junction and the depletion region of solar subcell similar to that of FIG. 1F depicting a graded band gap in that solar subcell according to a third embodiment of the present disclosure.

FIG. 2A is an enlarged view of the band diagram around the junction and the depletion region of solar subcell similar to that of FIG. 1F depicting a graded band gap in that solar subcell according to a third embodiment of the present disclosure in which the solar subcell is: (i) a homojunction; (ii) the band gap at the junction is greater than the band gap in both the n and p ungraded active region; (iii) the gradation in the hand gap is symmetric around the junction with the width of the graded region in the a region being equal to the width of the graded region in the p region; (iv) the depletion region is asymmetric around the junction; (v) the width of the depletion region is shorter in the a region than in die p region; and (vi) the aggregate width of the depletion region is equal to the width of the region with a gradation in band gap.

Although the illustration in FIG. 2A is an embodiment with characteristics (i) through (vi) above, the present disclosure contemplates further variants of characteristics (iv) through (vi) above in which: (iv) the depletion region is symmetric around the junction; (v) the width of the depletion region in the a region is longer than or equal to the width of the depletion region in the p region; and (vi) the aggregate width of the depletion region is longer than the width of the region with a gradation in band gap.

Figure 2B:
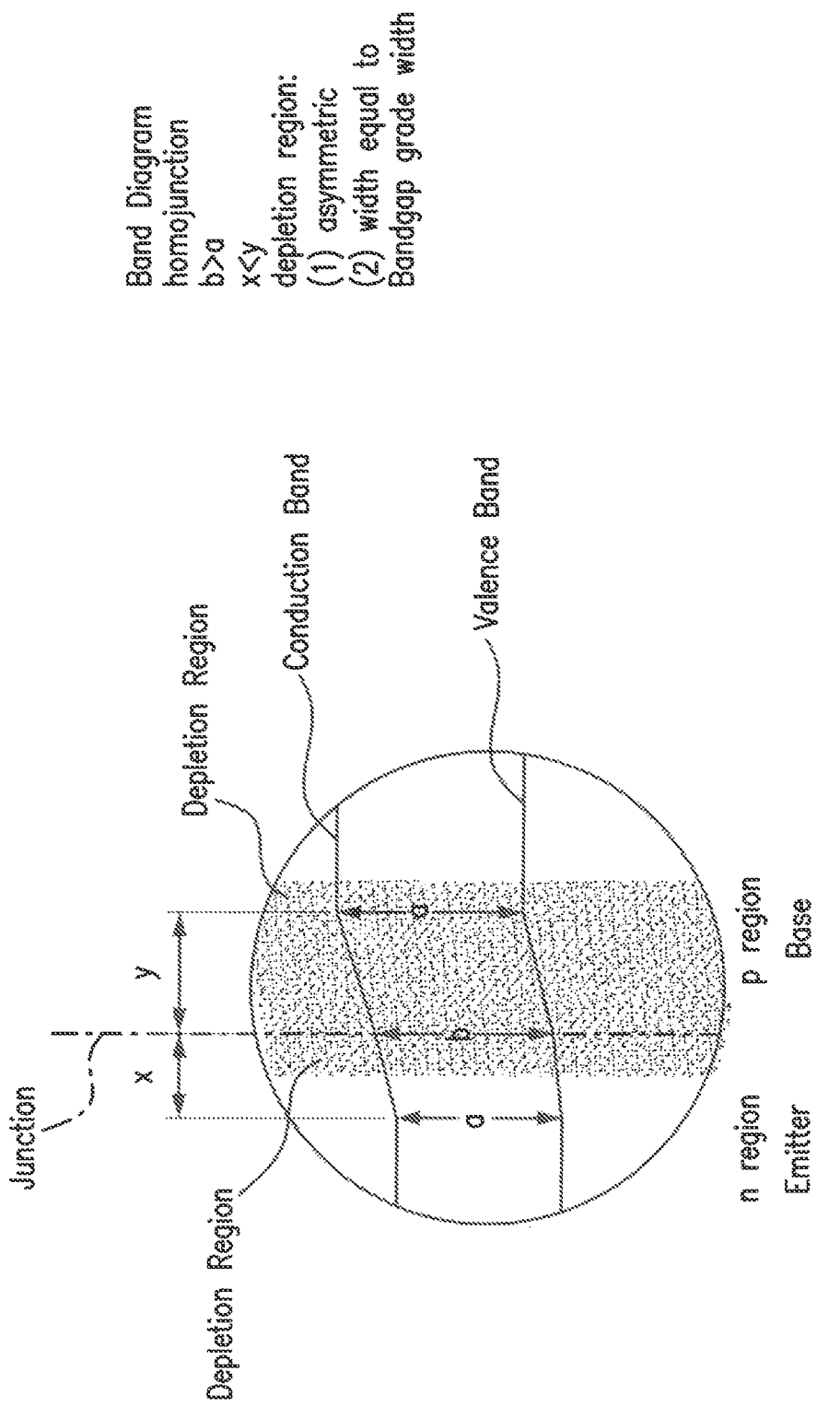
FIG. 2B is an enlarged view of the band diagram around the junction and depletion region of solar subcell similar to that of FIG. 1F depicting a graded band gap in that solar subcell according to a fourth embodiment of the present disclosure.

FIG. 2B is an enlarged view of the band diagram around the junction and the depletion region of solar subcell similar to that of FIG. 1F depicting a graded band gap in that solar subcell according to a fourth embodiment of the present disclosure in which the solar subcell is: (i) homojunction; (ii) the band gap at the junction is greater than the band gap in both the n and p ungraded active region; (iii) the gradation in the band gap is symmetric around the junction with the width of the graded region in the n region being equal to the width of the graded region in the p region; (iv) the depletion region is asymmetric around the junction; (v) the width of the depletion region is shorter in the n region than in the p region; and (vi) the aggregate width of the depletion region is equal to the width of the region with a gradation in hand gap.

Figure 2C:
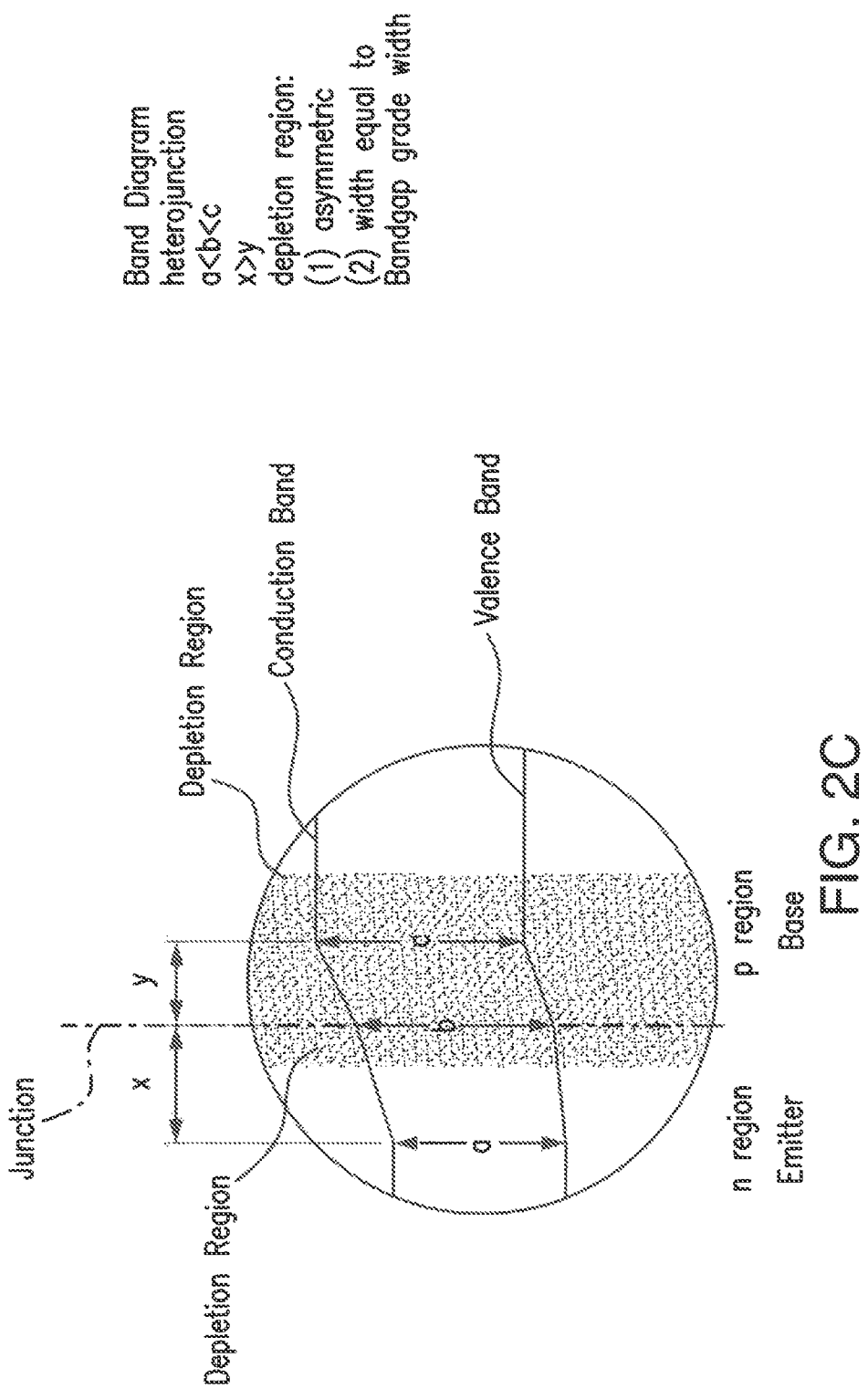
FIG. 2C is an enlarged view of the band diagram around the junction and depletion region of solar subcell similar to that of FIG. 1F depicting a graded band gap in that solar subcell according to a fifth embodiment of the present disclosure.

Although the illustration in FIG. 2B is an embodiment with characteristics (i) through (vi) above, the present disclosure contemplates further variants of characteristics (iii) through (vi) above in which: (iii) the gradation in band gap is asymmetric around the junction with the width of the graded region in the n region being longer than the width of the graded region in the p region (iv) the depletion region is symmetric around the junction; (v) the width of the depletion region in the ii region is longer than or equal to the width of the depletion region in the p region; and (vi) the aggregate width of the depletion region is longer than or shorter than the width of the region with a gradation in band gap, FIG. 2C is an enlarged view of the band diagram around the junction and the depletion region of solar subcell similar to that of FIG. 1F depicting a graded band gap in that solar subcell according to a fifth embodiment of the present disclosure in which the solar subcell is: (i) a heterojunction; (ii) the band gap at the junction is smaller than the band gap in both the n and p ungraded n region, and larger than the band gap in the ungraded p region; (iii) the gradation in the band gap is asymmetric around the junction with the width of the graded region in the n region being shorter than the width of the graded region in the p region; (iv) the depletion region is asymmetric around the junction; (v) the width of the depletion region is shorter in the n region than in the p region; and (vi) the aggregate width of the depletion region is equal to the width of the region with a gradation in band gap.

Although the illustration in FIG. 2C is an embodiment with Characteristics (i) through (vi) above, the present disclosure contemplates further variants of characteristics (iii) through (vi) above in which: (iii) the gradation in band gap is asymmetric around the junction with the width of the graded region in the n region being longer than the graded region in the p region (iv) the depletion region is symmetric around the junction; (v) the width of the depletion region in the n region is longer than or equal to the width of the depletion region in the p region; and (vi) the aggregate width of the depletion region is longer than or shorter than the width of the region with a gradation in band gap.

Figure 2D:
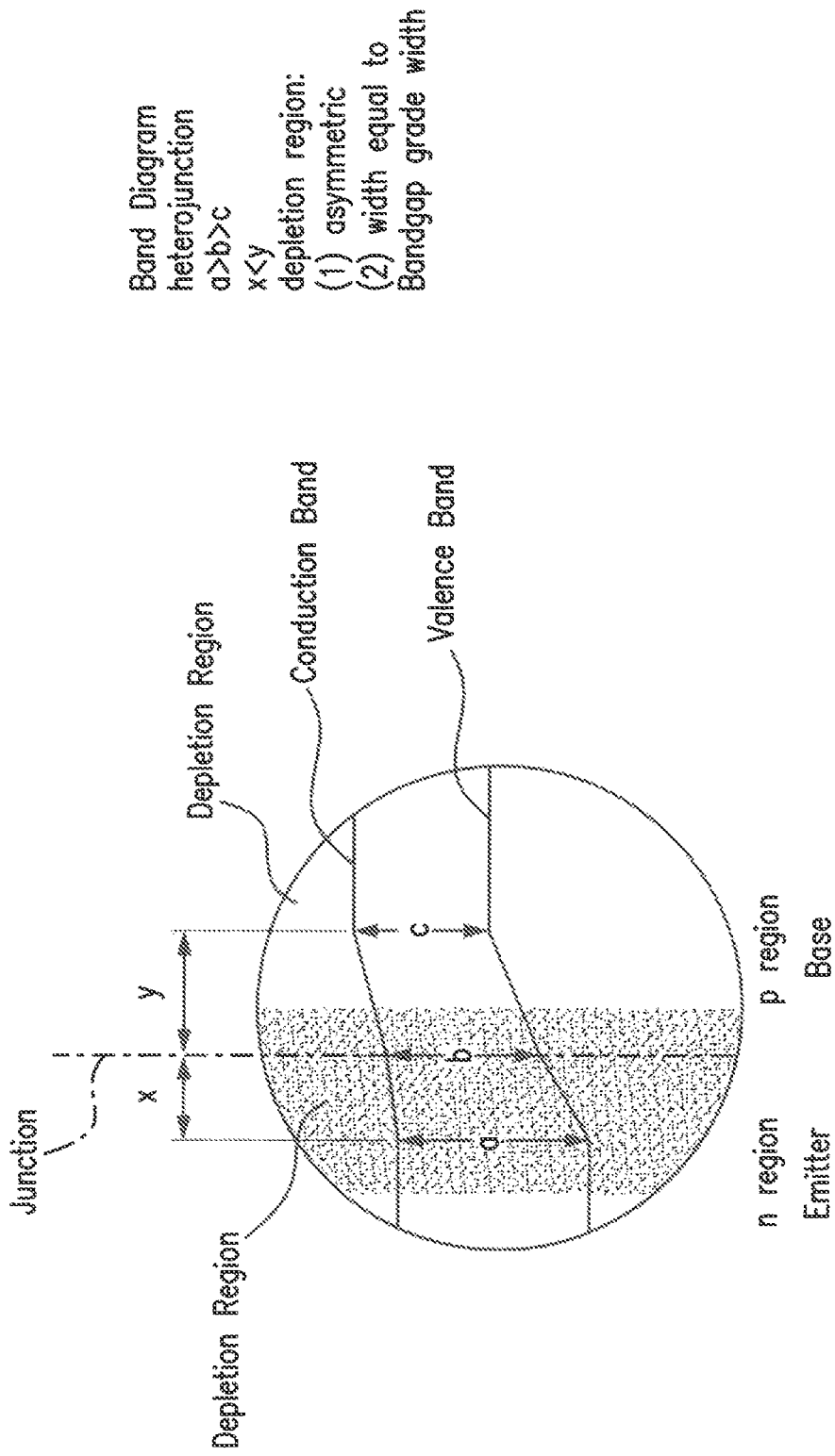
FIG. 2D is an enlarged view of the depletion region of solar subcell similar to that of FIG. 1F depicting a graded band gap in that solar subcell according to a sixth embodiment of the present disclosure.

FIG. 2D is an enlarged view of the band diagram around the junction and the depletion region of solar subcell similar to that of FIG. 1F depicting a graded band gap in that solar subcell according to a sixth embodiment of the present disclosure in which the solar subcell is: (i) heterojunction; (ii) the band gap at the junction is larger than the band gap in the ungraded n region, and smaller than the band gap in the ungraded p region; (iii) the gradation in the hand gap is asymmetric around the junction with the width of the graded region in then region being larger than the width of the graded region in the p region; (iv) the depletion region is asymmetric around the junction; (v) the width of the depletion region is longer in then region than in the p region; and (vi) the aggregate width of the depletion region is the same as the width of the region with a gradation in band gap, and typically extends a short distance into the base or p region.

Although the illustration in FIG. 2D is an embodiment with characteristics (i) though (vi) above, the present disclosure contemplates further variants of characteristics (iii) through (vi) above in which: (iii) the gradation in band gap is asymmetric around the junction with the width of the graded region in the n region being longer than the graded region in the p region (iv) the depletion region is symmetric around the junction; (v) the width of the depletion region ire the n region is longer than or equal to the width of the depletion region in the p region; and (vi) the aggregate width of the depletion region is shorter or longer than the width of the region with a gradation in band gap.

In some embodiments, in any of the illustrated examples above, the band gap may jump from one level to a higher band gap level at the junction, after which the band gap will remain constant at that level in the p-region.

To specifically depict a variety of different embodiments of multi junction solar cell devices in which the graded band gap of the present disclosure can be implemented, FIGS. 3A, 3B, 3C, 4, 5A, 5B and 6 are illustrative examples of such multifunction solar cells.

In FIGS. 3A, 3B, 3C, 4A, and 4B one or more of the solar subcells A, B, and C can incorporate the graded band gap according to the present disclosure, but since such details are described above, they will not be repeated in connection with each such Figure for the sake of brevity.

Figure 5A:
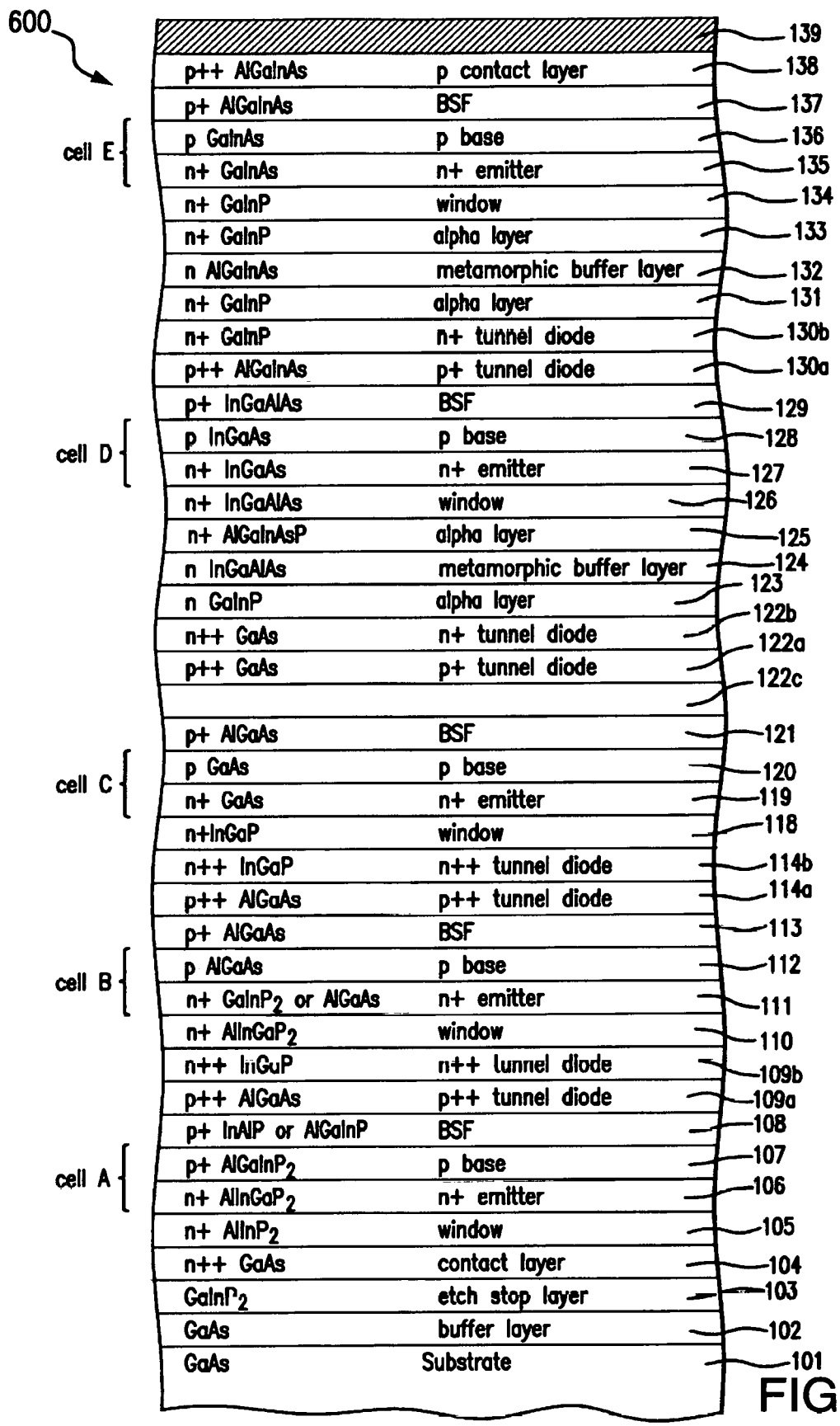
FIG. 5A is a cross-sectional view of a fifth embodiment of a solar cell according to the present disclosure after an initial stage of fabrication including the deposition of certain semiconductor layers on the growth substrate.

In FIGS. 5A, 5B, and 6 one or more of the solar subcells A, B, C, D, and E can incorporate the graded band gap according to the present disclosure, but since such details are described above, they will not be repeated in connection with each such Figure for the sake of brevity.

Figure 3A:
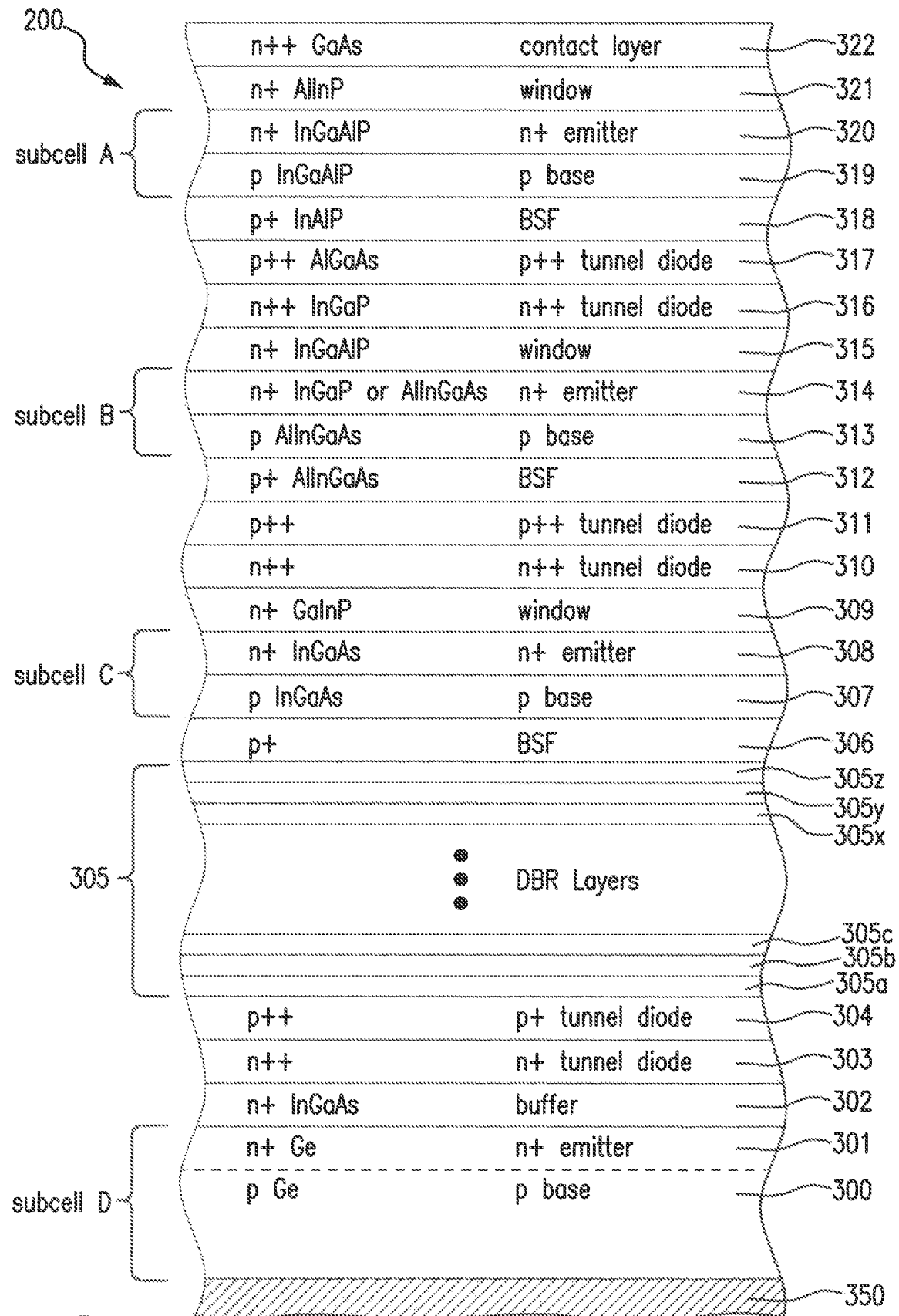
FIG. 3A is a cross-sectional view of a first embodiment of the solar cell according to the present disclosure that includes one distributed Bragg reflector (DBR) layer gown on top of the bottom subcell.

FIG. 3A is a cross-sectional view of an embodiment of a four junction solar cell 200 after several stages of fabrication including the growth of certain semiconductor layers on the growth substrate up to the contact layer 322 according to the present disclosure. In FIG. 3A, and in the solar cells depicted in FIGS. 3B, 4, 5 and 6, the graded band gap described above can be implemented in one or more of the solar subcells, but in the interest of brevity will not be repeated in the description of each of the embodiments the solar cells in such figures.

As shown in the illustrated example of FIG. 3A, the bottom subcell D includes a growth substrate 300 formed of p-type germanium ("Ge") which also serves as a base layer. A back metal contact pad 350 formed on the bottom of base layer 300 provides electrical contact to the multifunction solar cell 400. The bottom subcell D, further includes, for example, a highly doped n-type Ge emitter layer 301, and an n-type indium gallium arsenide ("InGaAs") nucleation layer 302. The nucleation layer is deposited over the base layer, and the emitter layer is formed in the substrate by diffusion of dopants into the Ge substrate, thereby forming the n-type Ge layer 301. Heavily doped p-type aluminum gallium arsenide ("AlGaAs") and heavily doped n-type gallium arsenide ("GaAs") tunneling junction layers 304, 303 may be deposited over the nucleation layer to provide a low resistance pathway between the bottom and middle subcells.

In some embodiments, Distributed Bragg reflector (DBR) layers 305 are then grown adjacent to and between the tunnel diode 303, 304 of the bottom subcell D and the third solar subcell C. The DBR layers 305 are arranged so that light can enter and pass through the third solar subcell C and at least a portion of which can be reflected back into the third solar subcell C by the DBR layers 305. In the embodiment depicted in FIG. 3, the distributed Bragg reflector (DBR) layers 305 are specifically located between the third solar subcell C and tunnel diode layers 304, 303; in other embodiments, the distributed Bragg reflector (DBR) layers may be located between tunnel diode layers 304/303 and buffer layer 302.

For some embodiments; distributed Bragg reflector (DBR) layers 305 can be composed of a plurality of alternating layers 305a through 305z of lattice matched materials with discontinuities in their respective indices of refraction. For certain embodiments, the difference in refractive indices between alternating layers is maximized in order to minimize the number of periods required to achieve a given reflectivity, and the thickness and refractive index of each period determines the stop band and its limiting wavelength.

For some embodiments, distributed Bragg reflector (DBR) layers 305a through 305z includes a first DBR layer composed of a plurality of p type $Al_xGa_{1-x}As$ layers, and a second DBR layer disposed over the first DBR layer and composed of a plurality of p type $Al_yGa_{1-y}As$ layers, where y is greater than x.

Although the present disclosure depicts the DBR layer 305 situated between the third and the fourth subcell, in other embodiments, DBR layers may be situated between the first and second subcells, and/or between the second and the third subcells, and/or between the third and the fourth subcells.

In the illustrated example of FIG. 3A, the subcell C includes a highly doped p-type aluminum gallium arsenide ("AlGaAs") back surface field ("BSF") layer 306, a p-type InGaAs base layer 307, a highly doped n-type indium gallium arsenide ("InGaAs") emitter layer 308 and a highly doped n-type indium aluminum phosphide ("AlInP2") or indium gallium phosphide ("GaInP") window layer 309. The InGaAs base layer 307 of the subcell C can include, for example, approximately 1.5% In. Other compositions may, be used as well. The base layer 307 is formed over the BSF layer 306 after the BSF layer is deposited over the DBR layers 305.

The window layer 309 is deposited on the emitter layer 308 of the subcell C. The window layer 309 in the subcell C also helps reduce the recombination loss and improves passivation of the cell surface of the underlying junctions. Before depositing the layers of the subcell B, heavily doped n-type InGaP and p-type AlGaAs (or other suitable compositions) tunneling junction layers 310, 311 may be deposited over the subcell C.

The second middle subcell B includes a highly doped p-type aluminum gallium arsenide ("AlGaAs") back surface field ("BSF") layer 312, a p-type AlGaAs base layer 313, a highly doped n-type indium gallium phosphide ("InGaP2") or AlGaAs layer 314 and a highly doped n-type indium gallium aluminum phosphide ("AlGaAlP") window layer 315. The InGaP emitter layer 314 of the subcell B can include, for example, approximately 50% In. Other compositions may be used as well.

Before depositing the layers of the top cell A, heavily doped n-type InGaP and p-type AlGaAs tunneling junction layers 316, 317 may be deposited over the subcell B.

In the illustrated example, the top subcell A includes a highly doped p-type indium aluminum phosphide ("InAlP2") BSF layer 318, a p-type InGaAlP base layer 319, a highly doped n-type InGaAlP emitter layer 320 and a highly doped n-type InAlP2 window layer 321. The base layer 319 of the top subcell A is deposited over the BSF layer 318 after the BSF layer 318 is formed.

After the cap or contact layer 322 is deposited, the grid lines are formed via evaporation and lithographically patterned and deposited over the cap or contact layer 322.

In some embodiments, at least the base of at least one of the first, second or third solar subcells has a graded doping, i.e., the level of doping varies from one surface to the other throughout the thickness of the base layer. In some embodiments, the gradation in doping is linear or exponential. In some embodiments, the gradation in doping is incremental and monotonic.

In some embodiments, the emitter of at least one of the first, second, or third solar subcells also has a graded doping, i.e., the level of doping varies from one surface to the other throughout the thickness of the emitter layer. In some embodiments, the gradation in doping is linear or monotonically increasing or decreasing.

In some embodiments, one or more of the subcells have a base region having a gradation in doping that increases from a value in the range of $1\times10^{15}$ to $1\times10^{18}$ free carriers per cubic centimeter adjacent the p-n junction to a value in the range of $1\times10^{16}$ to $4\times10^{18}$ free carriers per cubic centimeter adjacent to the adjoining layer at the rear of the base, and an emitter region having a gradation in doping that decreases from a value in the range of approximately $5 \times 10^{18}$ to $1 \times 10^{17}$ free carriers per cubic centimeter in the region immediately adjacent the adjoining layer to a value in the range of $5 \times 10^{15}$ to $1 \times 10^{18}$ free carriers per cubic centimeter in the region adjacent to the p-n junction.

Thus, the doping level throughout the thickness of the base layer may be exponentially graded from the range of $1 \times 10^{16}$ free carriers per cubic centimeter to $1 \times 10^{18}$ free carriers per cubic centimeter, as represented by the curve 603 depicted in the Figure.

Similarly, the doping level throughout the thickness of the emitter layer may decline linearly from $5 \times 10^{18}$ free carriers per cubic centimeter to $5 \times 10^{17}$ free carriers per cubic centimeter.

The absolute value of the collection field generated by an exponential doping gradient $\exp[-x/\lambda]$ is given by the constant electric field of magnitude $E = kT/q(1/\lambda)(\exp[-x_b/\lambda])$, where k is the Boltzman constant, T is the absolute temperature in degrees Kelvin, q is the absolute value of electronic change, and $\lambda$ is a parameter characteristic of the doping decay.

The efficacy of an embodiment of the doping arrangement present disclosure has been demonstrated in a test solar cell which incorporated an exponential doping profile in the three micron thick base layer a subcell, according to one embodiment.

The exponential doping profile taught by one embodiment of the present disclosure produces a constant field in the doped region. In the particular multijunction solar cell materials and structure of the present disclosure, the bottom subcell has the smallest short circuit current among all the subcells. Since in a multijunction solar cell, the individual subcells are stacked and form a series circuit, the total current flow in the entire solar cell is therefore limited by the smallest current produced in any of the subcells. Thus, by increasing the short circuit current in the bottom cell, the current more closely approximates that of the higher subcells, and the overall efficiency of the solar cell is increased as well. In a multifunction solar cell with approximately efficiency, the implementation of the present doping arrangement would thereby increase efficiency. In addition to an increase in efficiency, the collection field created by the exponential doping profile will enhance the radiation hardness of the solar cell, which is important for spacecraft applications.

Figure 3B:
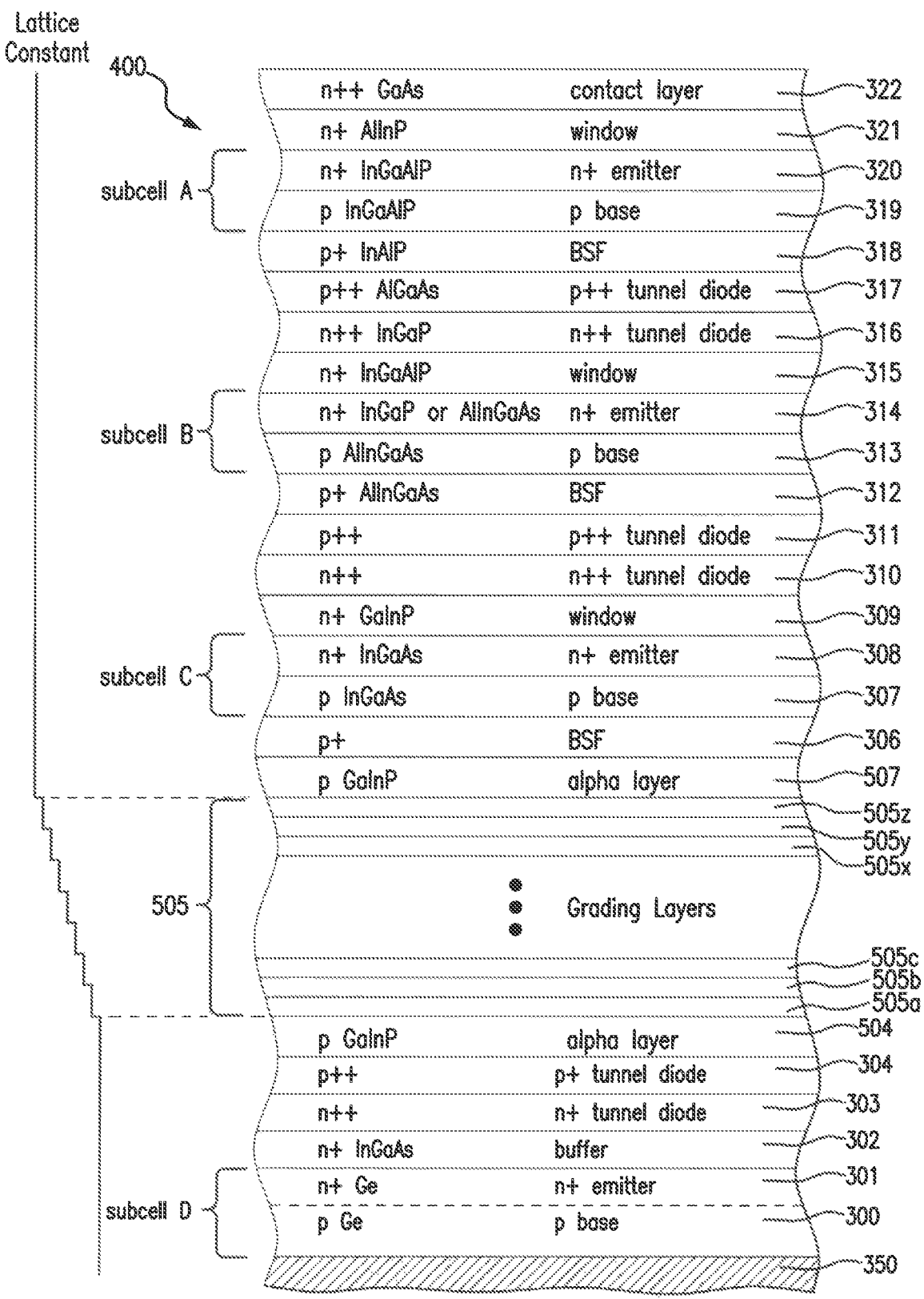
FIG. 3B is a cross-sectional view of a second embodiment of the solar cell according to the present disclosure that includes one grading or metamorphic layer grown on top of the bottom subcell.

FIG. 3B is a cross-sectional view of a second embodiment of a four junction solar cell 400 after several stages of fabrication including the growth of certain semiconductor layers on the growth substrate up to the contact layer 322, with various subcells being similar to the structure described and depicted in FIG. 3A. In the interest of brevity, the description of layers 350, 300 to 304, and 306 through 322 will not be repeated here.

In the embodiment depicted in FIG. 3B, an intermediate graded interlayer 505, comprising in one embodiment step-graded sublayers 505a through 505z, is disposed over the tunnel diode layer 304. In particular, the graded interlayer provides a transition in lattice constant from the lattice constant of the substrate to the larger lattice constant of the middle and upper subcells.

The graph on the left side of FIG. 3B depicts the in-plane lattice constant being incrementally monotonically increased from sublayer 505a through sublayer 505z, such sublayers being fully relaxed.

A metamorphic layer (or graded interlayer) 505 is deposited over the alpha layer 504 using a surfactant. Layer 505 is preferably a compositionally step-graded series of p-type InGaAs or InGaAlAs layers, preferably with monotonically changing lattice constant, so as to achieve a gradual transition in lattice constant in the semiconductor structure from subcell D to subcell C while minimizing threading dislocations from occurring. The band gap of layer 505 is constant throughout its thickness, preferably approximately equal to 1.22 to 1.34 eV, or otherwise consistent with a value slightly greater than the band gap of the middle subcell C. One embodiment of the graded interlayer may also be expressed as being composed of $In_xGa_{1-x}As$, with $0<x<1$, $0<y<1$, and x and y selected such that the band gap of the interlayer remains constant at approximately 1.22 to 1.34 eV or other appropriate band gap.

In one embodiment, aluminum is added to one sublayer to make one particular sublayer harder than another, thereby forcing dislocations in the softer layer.

In the surfactant assisted growth of the metamorphic layer 505, a suitable chemical element is introduced into the reactor during the growth of layer 505 to improve the surface characteristics of the layer. In the preferred embodiment, such element may be a dopant or donor atom such as selenium (Se) or tellurium (Te). Small amounts of Se or Te are therefore incorporated in the metamorphic layer 406, and remain in the finished solar cell. Although Se or Te are the preferred n-type dopant atoms, other nova-isoelectronic surfactants may be used as well.

Surfactant assisted growth results in a much smoother or planarized surface. Since the surface topography affects the bulk properties of the semiconductor material as it grows and the layer becomes thicker, the use of the surfactants minimizes threading dislocations in the active regions, and therefore improves overall solar cell efficiency.

As an alternative to the use of non-isoelectronic one may use an isoelectronic surfactant. The term "isoelectronic" refers to surfactants such as antimony (Sb) or bismuth (Bi), since such elements have the same number of valence electrons as the P atom of InGaP, or the As atom in InGaAlAs, in the metamorphic buffer layer. Such Sb or Bi surfactants will not typically be incorporated into the metamorphic layer 505.

In one embodiment of the present disclosure, the layer 505 is composed of a plurality of layers of InGaAs, with monotonically changing lattice constant, each layer having the same band gap, approximately in the range of 1.22 to 1.34 eV. In some embodiments, the constant band gap is in the range of 1.27 to 1.31 eV. In some embodiments, the constant hand gap is in the range of 1.28 to 1.29 eV.

The advantage of utilizing a constant bandgap material such as InGaAs is that arsenide-based semiconductor material is much easier to process in standard commercial MOCVD reactors.

Although the described embodiment of the present disclosure utilizes a plurality of layers of InGaAs for the metamorphic layer 505 for reasons of manufacturability and radiation transparency, other embodiments of the present disclosure may utilize different material systems to achieve a change in lattice constant from subcell C to subcell D. Other embodiments of the present disclosure may utilize continuously graded, as opposed to step graded, materials. More generally, the graded interlayer may be composed of any of the As, P, N, Sb based III-V compound semiconductors subject to the constraints of having the in-plane lattice parameter less than or equal to that of the third solar subcell C and greater than or equal to that of the fourth solar subcell D. In some embodiments, the layer 505 has a band gap energy greater than that of the third solar subcell C, and in other embodiments has a hand gap energy level less than that of the third solar subcell C.

In some embodiments, a second "alpha" or threading dislocation inhibition layer 506, preferably composed of p type GaInP, is deposited over metamorphic buffer layer 505, to a thickness of from 0.25 to about 1.0 micron. Such an alpha layer is intended to prevent threading dislocations from propagating, either opposite to the direction of growth into the subcell D, or in the direction of growth into the subcell C, and is more particularly described in U.S. Patent Application Pub. No. 2009/0078309 A1 (Cornfeld et al.).

Figure 3C:
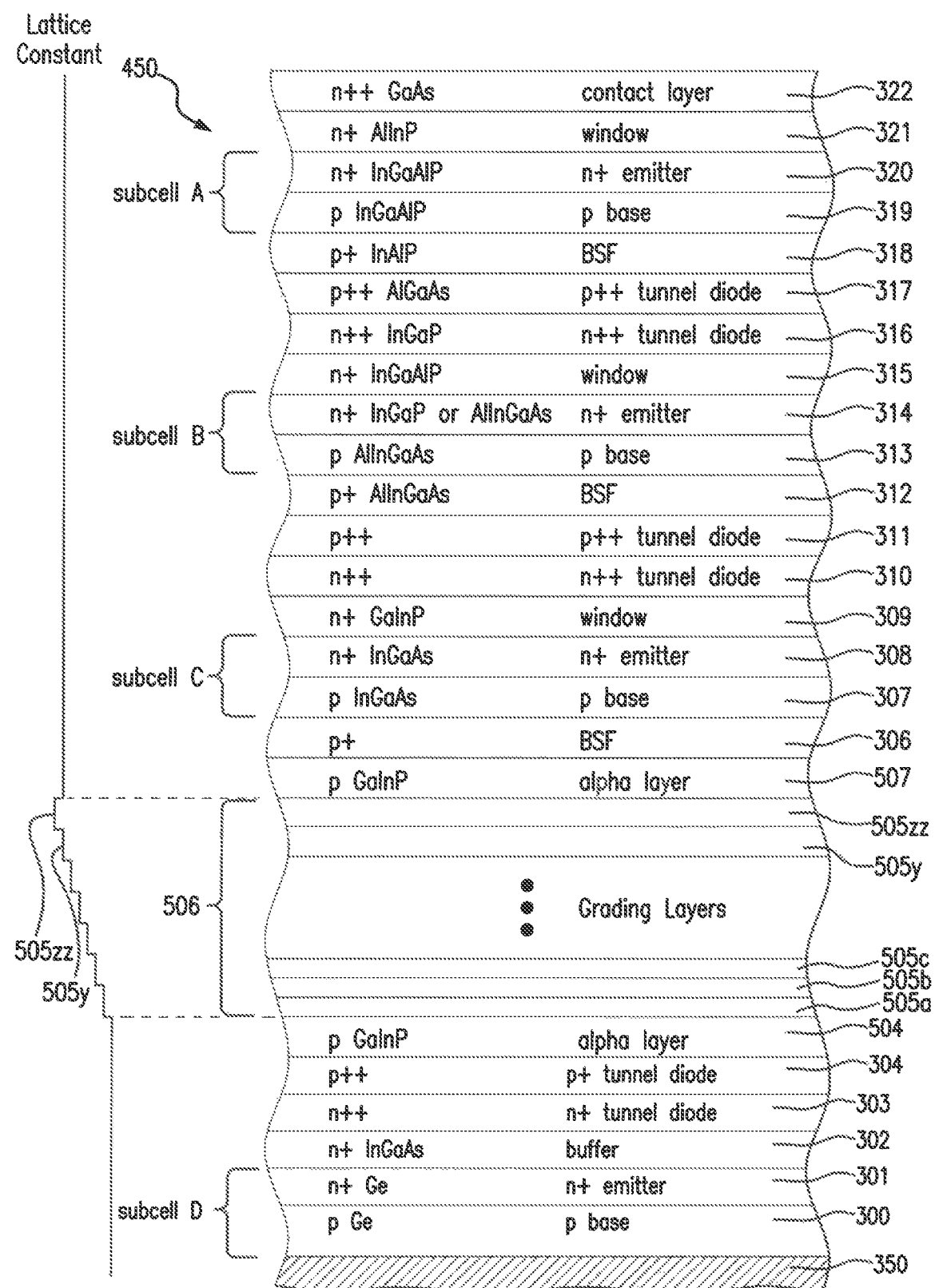
FIG. 3C is a cross-sectional view of a third embodiment of the solar cell according to the present disclosure that includes one grading or metamorphic layer gown on top of the bottom subcell.
Figure 4:
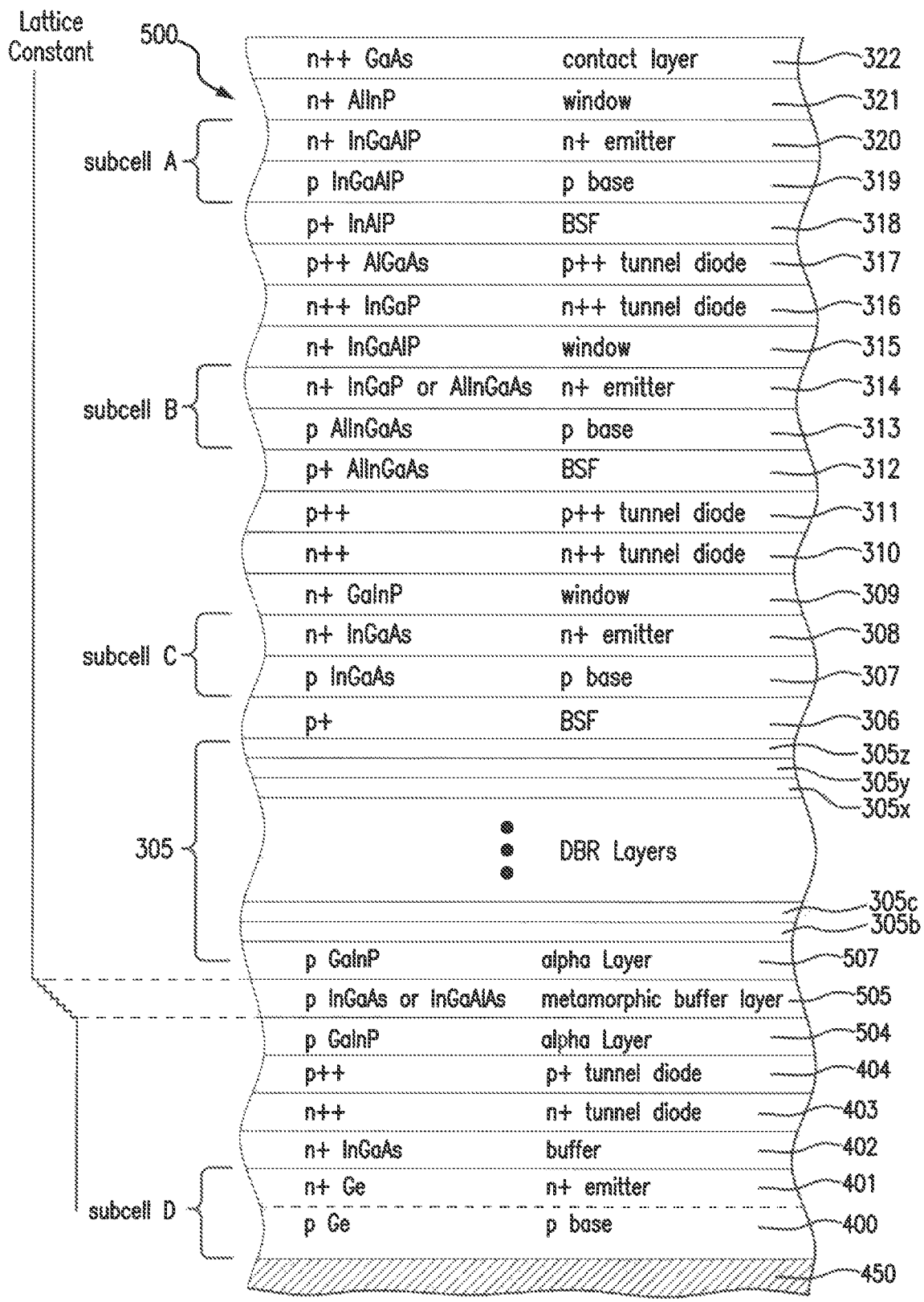
FIG. 4 is a cross-sectional view of a fourth embodiment of the solar cell according to the present disclosure that includes both a grading or metamorphic layer and a distributed Bragg reflector (DBR) layer gown on top of the bottom subcell.

In the third embodiment depicted in FIG. 3C, an intermediate graded interlayer 505, comprising in one embodiment step-graded sublayers 505a through 505zz, is disposed over the tunnel diode layer 304. In particular, the graded interlayer provides a transition in lattice constant from the lattice constant of the substrate to the larger lattice constant of the middle and upper subcells, and differs from that of the embodiment of FIG. 3A only in that the top or uppermost sublayer 505zz of the graded interlayer 506 is strained or only partially relaxed, and has a lattice constant which is greater than that of the layer above it, i.e., the alpha layer 506 (should there be a second alpha layer) or the BSF layer 306. In short, in this embodiment, there is an "overshoot" of the last one sublayer 505zz of the wading sublayers, as depicted on the left hand side of FIG. 4B, which shows the step-grading of the lattice constant becoming larger from layer 505a to 505zz, and then decreasing back to the lattice constant of the upper layers 506 through 322, FIG. 4 is a cross-sectional view of a fourth embodiment of a four junction solar cell 500 after several stages of fabrication including the growth of certain semiconductor layers on the growth substrate up to the contact layer 322, with various subcells being similar to the structure described and depicted in FIGS. 3A and 3B.

In this embodiment, both a grading interlayer 505 and a DBR layer 305 are disposed between subcell C and subcell D. The layers 450, 400 to 404, 504 to 506 and 306 through 322 are substantially similar to that of FIG. 2 and FIG. 3A or 3B and their description need not be repeated here.

In this embodiment, Distributed Bragg reflector (DBR) layers 305 are then grown adjacent to and over the alpha layer 506 (or the metamorphic buffer layer 505 if layer 506 is not present). The DBR layers 305 are arranged so that light can enter and pass through the third solar subcell C and at least a portion of Which can be reflected back into the third solar subcell C by the DBR layers 305. In the embodiment depicted in FIG. 5, the distributed Bragg reflector (DBR) layers 305 are specifically located between the third solar subcell C and metamorphic layer 505.

For some embodiments, distributed Bragg reflector (DBR) layers 305a through 305z includes a first DBR layer composed of a plurality of p type $Al_xGa_{1-x}As$ layers, and a second DBR layer disposed over the first DBR layer and composed of a plurality of p type $Al_yGa_{1-y}As$ layers, where y is greater than x.

The overall current produced by the multifunction cell solar cell may be raised by increasing the current produced by top subcell. Additional current can be produced by top subcell by increasing the thickness of the p-type $InGaAlP_2$ base layer in that cell. The increase in thickness allows additional photons to be absorbed, which results in additional current generation. Preferably, for space or AM0 applications, the increase in thickness of the top subcell maintains the approximately 4 to 5% difference in current generation between the top subcell A and middle subcell C. For AM1 or terrestrial applications, the current generation of the top cell and the middle cell may be chosen to be equalized.

Although FIGS. 3A, 3B, 3C, and 4 illustrate only four junction solar cells, the present disclosure also contemplates similar structures in two, three, five or six junction solar cells.

FIG. 5A depicts the "inverted metamorphic" multifunction solar cell according to a fifth embodiment of the present disclosure after the sequential formation of the five subcells A, B, C, D and F on a GaAs growth substrate. More particularly, there is shown a growth substrate 101, which is preferably gallium arsenide (GaAs), but may also be germanium (Ge) or other suitable material. For GaAs, the substrate is preferably a 15° off-cut substrate, that is to say, its surface is orientated 15° off the (100) plane towards the (111) A plane, as more fully described in U.S. Patent Application Pub. No. 2009/0229662 A1 (Stan et al.).

In the case of a Ge substrate, a nucleation layer (not shown) is deposited directly on the substrate 101. On the substrate, or over the nucleation layer (in the case of a Ge substrate), a buffer layer 102 and an etch stop layer 103 are further deposited. In the case of GaAs substrate, the buffer layer 102 is preferably GaAs. In the case of Ge substrate, the buffer layer 102 is preferably InGaAs. A contact layer 104 of GaAs is then deposited on layer 103, and a window layer 105 of AlInP is deposited on the contact layer. The subcell A, consisting of an n+ emitter layer 106 and a p-type base layer 107, is then epitaxially deposited on the window layer 105. The subcell A is generally latticed matched to the growth substrate 101.

It should be noted that the multijunction solar cell structure could be formed by any suitable combination of group III to V elements listed in the periodic table subject to lattice constant and bandgap requirements, wherein the group III includes boron (B), aluminum (Al), gallium (Ga), indium (In), and thallium (T). The group IV includes carbon (C), silicon (Si), germanium (Ge), and tin (Sn). The group V includes nitrogen (N), phosphorous (P), arsenic (As), antimony (Sb), and bismuth (Bi).

In one embodiment, the emitter layer 106 is composed of $InGa(Al)P_2$ and the base layer 107 is composed of $InGa(Al)P_2$. The aluminum or Al term in parenthesis in the preceding formula means that Al is an optional constituent, and in this instance may be used in an amount ranging from 0% to 40%.

Subcell A will ultimately become the "top" subcell of the inverted metamorphic structure after completion of the process steps according to the present disclosure to be described hereinafter.

On top of the base layer 107 a back surface field ("BST") layer 108 preferably p+ AlGaInP is deposited and used to reduce recombination loss.

The BSF layer 108 drives minority carriers from the region near the base/BSF interface surface to minimize the effect of recombination loss. In other words, a BSF layer 108 reduces recombination loss at the backside of the solar subcell A and thereby reduces the recombination in the base.

On top of the BSF layer 108 is deposited a sequence of heavily doped p-type and n-type layers 109a and 109b that forms a tunnel diode, i.e., an ohmic circuit element that connects subcell A to subcell B. Layer 109a is preferably composed of p++ AlGaAs, and layer 109b is preferably composed of n++ InGaP.

A window layer 110 is deposited on top of the tunnel diode layers 109a/109b, and is preferably n+ InGaP. The advantage of utilizing InGaP as the material constituent of the window layer 110 is that it has an index of refraction that closely matches the adjacent emitter layer 111, as more fully described in U.S. Patent Application Pub. No. 2009/0272430 A1 (Cornfeld et al.). The window layer 110 used in the subcell B also operates to reduce the interface recombination loss. It should be apparent to one skilled in the art, that additional layer(s) may be added or deleted in the cell structure without departing from the scope of the present disclosure.

On top of the window layer 110 the layers of subcell B are deposited: the n-type emitter layer 111 and the p-type base layer 112. These layers are preferably composed of InGaP and AlInGaAs respectively (for a Ge substrate or growth template), or InGaP and AlGaAs respectively (for a GaAs substrate), although any other suitable materials consistent with lattice constant and bandgap requirements may be used as well. Thus, subcell B may be composed of a GaAs, InGaP, AlGaInAs, AlGaAsSb, GaInAsP, AlGaInAsP, emitter region and a GaAs, InGaP, AlGaInAs, AlGaAsSb, GaInAsP, or AlGaInAsP base region.

In previously disclosed implementations of an inverted metamorphic solar cell, the second subcell or subcell B or was a homostructure. In the present disclosure, similarly to the structure disclosed in U.S. Patent Application Pub. No. 2009/0078310 A1 (Stan et al.), the second subcell or subcell B becomes a heterostructure with an InGaP emitter and its window is converted from InAlP to AlInGaP. This modification reduces the refractive index discontinuity at the window/emitter interface of the second subcell, as more fully described in U.S. Patent Application Pub. No. 2009/0272430 A1 (Cornfeld et al.). Moreover, the window layer 110 is preferably is doped three times that of the emitter 111 to move the Fermi level up closer to the conduction band and therefore create band bending at the window/emitter interface which results in constraining the minority carriers to the emitter layer.

On top of the cell B is deposited a BSF layer 113 which performs the same function as the BSF layer 109. The p++/n++ tunnel diode layers 114a and 114b respectively are deposited over the BSF layer 113, similar to the layers 109a and 109b, forming an ohmic circuit element to connect subcell B to subcell C. The layer 114a is preferably composed of p++ AlGaAs, and layer 114b is preferably composed of n++ InGaP.

A window layer 118 preferably composed of n+ type GaInP is then deposited over the tunnel diode layer 114. This window layer operates to reduce the recombination loss in subcell "C", It should be apparent to one skilled in the art that additional layers may be added or deleted in the cell structure without departing from the scope of the present disclosure.

On top of the window layer 118, the layers of cell C are deposited: the n+ emitter layer 119, and the p-type base layer 120. These layers are preferably composed of n+ type GaAs and n+ type GaAs respectively, or n+ type InGaP and p type GaAs for a heterojunction subcell, although another suitable materials consistent with lattice constant and bandgap requirements may be used as well.

In some embodiments, subcell C may be (In)GaAs with a band gap between 1.40 eV and 1.42 eV. Grown in this manner, the cell has the same lattice constant as GaAs but has a low percentage of Indium 0%<In<1% to slightly lower the band gap of the subcell without causing it to relax and create dislocations. In this case, the subcell remains lattice matched, albeit strained, and has a lower band gap than GaAs. This helps improve the subcell short circuit current slightly and improve the efficiency of the overall solar cell.

In some embodiments, the third subcell or subcell C may have quantum wells or quantum dots that effectively lower the band gap of the subcell to approximately 1.3 eV. All other band gap ranges of the other subcells described above remain the same. In such embodiment, the third subcell is still lattice matched to the GaAs substrate. Quantum wells are typically "strain balanced" by incorporating lower band gap or larger lattice constant InGaAs (e.g. a band gap of ~1.3 eV) and higher band gap or smaller lattice constant GaAsP. The larger/smaller atomic lattices/layers of epitaxy balance the strain and keep the material lattice matched.

A BSF layer 121, preferably composed of InGaAlAs, is then deposited on top of the cell C, the BSF layer performing the same function as the BSF layers 108 and 113.

The p++/n++ tunnel diode layers 122a and 122b respectively are deposited over the BSF layer 121, similar to the layers 114a and 114b, forming an ohmic circuit element to connect subcell C to subcell D. The layer 122a is preferably composed of p++ GaAs, and layer 122b is preferably composed of n++ GaAs.

An alpha layer 123, preferably composed of n-type GaInP, is deposited over the tunnel diode 122a/122b, to a thickness of about 1.0 micron. Such an alpha layer is intended to prevent threading dislocations from propagating, either opposite to the direction of growth into the top and middle subcells A, B and C, or in the direction of growth into the subcell D, and is more particularly described in U.S. Patent Application Pub. No. 2009/0078309 A1 (Cornfeld et al.).

A metamorphic layer (or graded interlayer) 124 is deposited over the alpha layer 123 using a surfactant. Layer 124 is preferably a compositionally step-graded series of InGaAlAs layers, preferably with monotonically changing lattice constant, so as to achieve a gradual transition in lattice constant in the semiconductor structure from subcell C to subcell D while minimizing threading dislocations from occurring. The band gap of layer 124 is constant throughout its thickness, preferably approximately equal to 1.5 to 1.6 eV, or otherwise consistent with a value slightly greater than the band gap of the middle subcell C. One embodiment of the graded interlayer may also be expressed as being composed of $(In_xGa_{1-x})_yAl_{1-y}As$, with x and y selected such that the band gap of the interlayer remains constant at approximately 1.5 to 1.6 eV or other appropriate band gap.

In the surfactant assisted growth of the metamorphic layer 124, a suitable chemical element is introduced into the reactor during the growth of layer 124 to improve the surface characteristics of the layer. In the preferred embodiment, such element may be a dopant or donor atom such as selenium (Se) or tellurium (Te). Small amounts of Se or Te are therefore incorporated in the metamorphic layer 124, and remain in the finished solar cell. Although Se or Te are the preferred n-type dopant atoms, other non-isoelectronic surfactants may be used as well.

Surfactant assisted growth results in a much smoother or planarized surface. Since the surface topography affects the bulk properties of the semiconductor material as it grows and the layer becomes thicker, the use of the surfactants minimizes threading dislocations in the active regions, and therefore improves overall solar cell efficiency.

As an alternative to the use of non-isoelectronic one may use an isoelectronic surfactant. The term "isoelectronic" refers to surfactants such as antimony (Sb) or bismuth (Bi), since such elements have the same number of valence electrons as the P atom of InGaP, or the As atom in InGaAlAs, in the metamorphic buffer layer. Such Sb or Bi surfactants will not typically be incorporated into the metamorphic layer 124.

In the inverted metamorphic structure described in the Wanlass et al. paper cited above, the metamorphic layer consists of nine compositionally graded InGaP steps, with each step layer having a thickness of 0.25 micron. As a result, each layer of Wanlass et al. has a different bandgap. In one of the embodiments of the present disclosure, the layer 124 is composed of a plurality of layers of InGaAlAs, with monotonically changing lattice constant, each layer having the same band gap, approximately in the range of 1.5 to 1.6 eV.

The advantage of utilizing a constant bandgap material such as InGaAlAs is that arsenide-based semiconductor material is much easier to process in standard commercial MOCVD reactors, while the small amount of aluminum assures radiation transparency of the metamorphic layers.

Although the preferred embodiment of the present disclosure utilizes a plurality of layers of InGaAlAs for the metamorphic layer 124 for reasons of manufacturability and radiation transparency, other embodiments of the present disclosure may utilize different material systems to achieve a change in lattice constant from subcell C to subcell D. Thus, the system of Wanlass using compositionally graded InGaP is a second embodiment of the present disclosure. Other embodiments of the present disclosure may utilize continuously graded, as opposed to step graded, materials. More generally, the graded interlayer may be composed of any of the As, P, N, Sb based III-V compound semiconductors subject to the constraints of having the in-plane lattice parameter greater than or equal to that of the second solar cell and less than or equal to that of the third solar cell, and having a bandgap energy greater than that of the second solar cell.

An alpha layer 125, preferably composed of n+ type AlGaInAsP, is deposited over metamorphic buffer layer 124, to a thickness of about 1.0 micron. Such an alpha layer is intended to prevent threading dislocations from propagating, either opposite to the direction of growth into the top and middle subcells A, B and C, or in the direction of growth into the subcell D, and is more particularly described in U.S. Patent Application Pub. No. 2009/0078309 A1 (Cornfield et al.).

A window layer 126 preferably composed of n+ type InGaAlAs is then deposited over alpha layer 125. This window layer operates to reduce the recombination loss in the fourth subcell "D". It should be apparent to one skilled in the art that additional layers may be added or deleted in the cell structure without departing from the scope of the present disclosure.

On top of the window layer 126, the layers of cell D are deposited: the n+ emitter layer 127, and the p-type base layer 128. These layers are preferably composed of n+ type InGaAs and p type InGaAs respectively, or n+ type InGaP and p type InGaAs for a heterojunction although another suitable materials consistent with lattice constant and bandgap requirements may be used as well.

A BSF layer 129, preferably composed of p+ type InGaAlAs, is then deposited on top of the cell D, the BSF layer performing the same function as the BSF layers 108, 113 and 121:

The p++/n++ tunnel diode layers 130a and 130h respectively are deposited over the BSF layer 129, similar to the layers 122a/122b and 109a/109h, forming an ohmic circuit element to connect subcell D to subcell E. The layer 130a is preferably composed of p++ AlGaInAs, and layer 130b is preferably composed of n++ GaInP.

In some embodiments an alpha layer 131, preferably composed of n-type GaInP, is deposited over the tunnel diode 130a/130b, to a thickness of about 0.5 micron. Such alpha layer is intended to prevent threading dislocations from propagating, either opposite to the direction of growth into the middle subcells C and D, or in the direction of growth into the subcell E, and is more particularly described in copending U.S. patent application Ser. No. 11/860,183, filed Sep. 24, 2007.

A second metamorphic layer (or graded interlayer) 132 is deposited over the barrier layer 131. Layer 132 is preferably a compositionally step-graded series of AlGaInAs layers, preferably with monotonically changing lattice constant, so as to achieve a gradual transition in lattice constant in the semiconductor structure from subcell D to subcell P while minimizing threading dislocations from occurring. In some embodiments the band gap of layer 132 is constant throughout its thickness, preferably approximately equal to 1.1 eV, or otherwise consistent with a value slightly greater than the band gap of the middle subcell D. One embodiment of the graded interlayer may also be expressed as being composed of $(In_xGa_{1-x})_y Al_{1-y}As$, with $0<x<1$, $0<y<1$, and x and y selected such that the band gap of the interlayer remains constant at approximately 1.1 eV or other appropriate band gap.

In one embodiment of the present disclosure, an optional second barrier layer 133 may be deposited over the AlGaInAs metamorphic layer 132. The second barrier layer 133 performs essentially the same function as the first barrier layer 131 of preventing threading dislocations from propagating. In one embodiment, barrier layer 133 has not the same composition than that of barrier layer 131, i.e. n+ type GaInP.

A window layer 134 preferably composed of n+ type GaInP is then deposited over the barrier layer 133. This window layer operates to reduce the recombination loss in the fifth subcell "E". It should be apparent to one skilled in the art that additional layers may be added or deleted in the cell structure without departing from the scope of the present invention.

On top of the window layer 134, the layers of cell E are deposited: the n+ emitter layer 135, and the p-type base layer 136. These layers are preferably composed of n+ type GaInAs and p type GaInAs respectively, although other suitable materials consistent with lattice constant and hand gap requirements may be used as well.

A BSF layer 137, preferably composed of p+ type AlGaInAs, is then deposited on top of the cell E, the BSF layer performing the same function as the BSF layers 108, 113, 121, and 129.

Finally, a high hand gap contact layer 138, preferably composed of p++ type AlGaInAs, is deposited on the BSF layer 137.

The composition of this contact layer 138 located at the bottom (non-illuminated) side of the lowest band gap photovoltaic cell (i.e., subcell "E" in the depicted embodiment) in a multijunction photovoltaic cell, can be formulated to reduce absorption of the light that passes through the cell, so that (i) the backside ohmic metal contact layer below it (on the non-illuminated side) will also act as a mirror layer, and (ii) the contact layer doesn't have to be selectively etched off, to prevent absorption.

It should be apparent to one skilled in the art, that additional layer(s) may be added or deleted in the cell structure without departing from the scope of the present invention.

A metal contact layer 139 is deposited over the p semiconductor contact layer 138. The metal is the sequence of metal layers Ti/Au/Ag/Au in some embodiments.

The metal contact scheme chosen is one that has a planar interface with the semiconductor, after heat treatment to activate the ohmic contact. This is done so that (1) a dielectric layer separating the metal from the semiconductor doesn't have to be deposited and selectively etched in the metal contact areas; and (2) the contact layer is secularly reflective over the wavelength range of interest.

Optionally, an adhesive layer (e.g., Wafer Bond, manufactured by Brewer Science, Inc. of Rolla, Mo.) can be deposited over the metal layer 131, and a surrogate substrate can be attached. In some embodiments, the surrogate substrate may be sapphire. In other embodiments, the surrogate substrate may be GaAs, Ge or Si, or other suitable material. The surrogate substrate can be about 40 mils in thickness, and can be perforated with holes about 1 mm in diameter, spaced 4 mm apart, to aid in subsequent removal of the adhesive and the substrate. As an alternative to using an adhesive layer, a suitable substrate (e.g., GaAs) may be eutectically or permanently bonded to the metal layer 131.

Optionally, the original substrate can be removed by a sequence of lapping and/or etching steps in which the substrate 101, and the buffer layer 102 are removed. The choice of a particular etchant is growth substrate dependent.

FIG. 5B is a cross-sectional view of an embodiment of a solar cell similar to that in FIG. 5A, with the orientation with the metal contact layer 139 being at the bottom of the Figure and with the original substrate having been removed. In addition, the etch stop layer 103 has been removed, for example, by using a HCl/H2O solution.

It should be apparent to one skilled in the art, that additional layer(s) may be added or deleted in the cell structure without departing from the scope of the present disclosure. For example, one or more distributed Bragg reflector (DBR) layers can be added for various embodiments of the present invention.

FIG. 6 is a cross-sectional view of a sixth embodiment of a solar cell similar to that of FIGS. 5A and 5B that includes distributed Bragg reflector (DBR) layers 122c adjacent to and between the third solar subcell C and the graded interlayer 124 and arranged so that light can enter and pass through the third solar subcell C and at least a portion of which can be reflected back into the third solar subcell C by the DBR layers 122c. In FIG. 6, the distributed Bragg reflector (DBR) layers 122c are specifically located between the third solar subcell C and tunnel diode layers 122a/122b.

FIG. 6 also includes distributed Bragg reflector (DBR) layers 114c adjacent to and between the second solar subcell B and the subcell C and arranged so that light can enter and pass through the second solar subcell B and at least a portion of which can be reflected back into the second solar subcell B by the DBR layers 114c. In FIG. 6, the distributed Bragg reflector (DBR) layers 114c are specifically located between subcell B and tunnel diode layers 114a/114b.

For some embodiments, distributed Bragg reflector (DBR) layers 114c and/or 122c can be composed of a plurality of alternating layers of lattice matched materials with discontinuities in their respective indices of refraction. For certain embodiments, the difference in refractive indices between alternating layers is maximized in order to minimize the number of periods required to achieve a given reflectivity, and the thickness and refractive index of each period determines the stop band and its limiting wavelength.

For some embodiments, distributed Bragg reflector (DBR) layers 114c and/or 122c includes a first DBR layer composed of a plurality of p type $Al_xGa_{1-x}As$ layers, and a second DBR layer disposed over the first DBR layer and composed of a plurality of p type $Al_yGa_{1-y}As$ layers, where y is greater than x, and $0<x<1$, $0<y<1$.

In addition to the gradation in band gap in one or more subcells, for some embodiments, the present disclosure provides metamorphic multijunction solar cell that follows a design rule that one should incorporate as many high bandgap subcells as possible to achieve the goal to increase high temperature EOL performance as set fourth in related applications of Applicant. For example, high bandgap subcells may retain a greater percentage of cell voltage as temperature increases, thereby offering lower power loss as temperature increases. As a result, both HT-BOL and HT-EOL performance of the exemplary metamorphic multijunction solar cell may be expected to be greater than traditional cells.

Measurements of the external quantum efficiency of a AlGaAs subcell indicates that an AlGaAs subcell (which may typically be of composition of the second, third, or lower subcell in a multijunction solar cell) has minority carrier diffusion length $L_{min}$ of 3.5 µm for a solar subcell subject to radiation exposure and damage, compared to 3.0 µm for a similar solar subcell with a constant or non-graded band gap, demonstrating the efficiency of the use of a graded band gap as taught by the present disclosure.

For example, the cell efficiency (%) measured at room temperature (RT) 28° C. and high temperature (HT) 70° C., at beginning of life (BOL) and end of life (EOL), for a standard three junction commercial solar cell (ZTJ) is as follows:

| | | |
|---|---|---|
| BOL 28° C. | 29.1% | |
| BOL 70° C. | 26.4% | |
| EOL 70° C. | 23.4% | After $5E14$ e/cm$^2$ radiation |
| EOL 70° C. | 22.0% | After $1E15$ e/cm$^2$ radiation |

For the four junction IMMX solar cell described in the related application, the corresponding data is as follows:

| Condition | Efficiency | |
|---|---|---|
| BOL 28° C. | 29.5% | |
| BOL 70° C. | 26.6% | |
| EOL 70° C. | 24.7% | After $5E14$ e/cm$^2$ radiation |
| EOL 70° C. | 24.2% | After $1E15$ e/cm$^2$ radiation |

One should note the slightly higher cell efficiency of the IMMX solar cell than the standard commercial solar cell (ZTJ) at BOL both at 28° C. and 70° C. However, the IMMX solar cell described above exhibits substantially improved cell efficiency (%) over the standard commercial solar cell (ZTJ) at 1 MeV electron equivalent thence of $5\times10^{14}$ e/cm$^2$, and dramatically improved cell efficiency (%) over the standard commercial solar cell (ZTJ) at 1 MeV electron equivalent fluence of $1\times10^{15}$ e/cm$^2$.

For one embodiment of a five junction IMMX solar cell described in the related application, the corresponding data is as follows:

| Condition | Efficiency | |
|---|---|---|
| BOL 28° C. | 33.1% | |
| BOL 70° C. | 30.4% | |
| EOL 70° C. | 27.1% | After $5E14$ e/cm$^2$ radiation |
| EOL 70° C. | 25.8% | After $1E15$ e/cm$^2$ radiation |

In addition to the high temperature (HJ) applications described above, in some embodiments, solar cells with a graded band gap according to the present disclosure are also applicable to low intensity (LI) and/or low temperature (LT) environments, such as might be experienced in space vehicle missions to Mars, Jupiter, the Europa moon of Jupiter, and beyond. A "low intensity" environment refers to a light intensity being less than 0.1 suns, and a "low temperature" environment refers to temperatures being in the range of less than minus 100 degrees Centigrade.

For such applications, depending upon the specific intensity and temperature ranges of interest, the band gaps of the subcells may be adjusted or "tuned" to maximize the solar cell efficiency, or otherwise optimize performance (e.g. at EOL or over the operational working life period).

In view of different satellite and space vehicle requirements in terms of operating environmental temperature, radiation exposure, and operational life, a range of subcell designs using the design principles of the present disclosure may be provided satisfying specific defined customer and mission requirements, and several illustrative embodiments are set forth hereunder, along with the computation of their efficiency at the end-of-life for comparison purposes. As described in greater detail below, solar cell performance after radiation exposure is experimentally measured using 1 MeV electron fluence per square centimeter (abbreviated in the text that follows as e/cm$^2$), so that a comparison can be made between the current commercial devices and embodiments of solar cells discussed in the present disclosure.

As an example of different mission requirements, a low earth orbit (LEO) satellite will typically experience radiation of protons equivalent to an electron fluence per square centimeter in the range of 1×10$^{12}$ e/cm$^2$ to 2×10$^{14}$ e/cm$^2$ (hereinafter may be written as "2E10 e/cm$^2$ or 2E14") over a five year lifetime. A geosynchronous earth orbit (GEO) satellite will typically experience radiation in the range of 5×10$^{14}$ e/cm$^2$ to 1×10$^{15}$ e/cm$^2$ over a fifteen year lifetime.

The solar cells of the present application may be adjusted or turned to operate optimally in either such earth orbit, or on space missions to Mars or Jupiter with LI and LT environments.

The wide range of electron and proton energies present in the space environment necessitates a method of describing the effects of various types of radiation in terms of a radiation environment which can be produced under laboratory conditions. The methods for estimating solar cell degradation in space are based on the techniques described by Brown et al. [Brown, W. L., J. D. Gabbe, and W. Rosenzweig, Results of the Telstar Radiation Experiments, Bell System Technical J., 42, 1505, 1963] and Tada [Tada, H. Y., J. R. Carter, Jr., B. E. Anspaugh, and R. G. Downing, Solar Cell Radiation Handbook, Third Edition, JPL Publication 82-69, 1982]. In summary, the omnidirectional space radiation is converted to a damage equivalent unidirectional fluence at a normalised energy and in terms of a specific radiation particle. This equivalent fluence will produce the same damage as that produced by omnidirectional space radiation considered When the relative damage coefficient (RDC) is properly defined to allow the conversion. The relative damage coefficients (RDCs) of a particular solar cell structure are measured a priori under many energy and fluence levels in addition to different coverglass thickness values. When the equivalent fluence is determined for a given space environment, the parameter degradation can be evaluated in the laboratory by irradiating the solar cell with the calculated fluence level of unidirectional normally incident flux. The equivalent fluence is normally expressed in terms of 1 MeV electrons or 10 MeV protons.

The software package Spenvis (www.spenvis.oma.be) is used to calculate the specific electron and proton fluence that a solar cell is exposed to during a specific satellite mission as defined by the duration, altitude, azimuth, etc. Spenvis employs the EQFLUX program, developed by the Jet Propulsion Laboratory (JPL) to calculate 1 MeV and 10 MeV damage equivalent electron and proton fluences, respectively, for exposure to the fluences predicted by the trapped radiation and solar proton models for a specified mission environment duration. The conversion to damage equivalent fluences is based on the relative damage coefficients determined for multifunction cells [Marvin, D. C., Assessment of Multifunction Solar Cell Performance in Radiation Environments, Aerospace Report No. TOR-2000 (1210)-1, 2000]. New cell structures eventually need new RDC measurements as different materials can be more or less damage resistant than materials used in conventional solar cells. A widely accepted total mission equivalent fluence for a geosynchronous satellite mission of 15 year duration is MeV 1×10$^{15}$ electrons/cm$^2$.

The exemplary solar cell described herein may require the use of aluminum in the semiconductor composition of each of the top two or three subcells. Aluminum incorporation is widely known in the III-V compound semiconductor industry to degrade BOIL subcell performance due to deep level donor defects, higher doping compensation, shorter minority carrier lifetimes, and lower cell voltage and an increased BOL $E_g$-$V_{oc}$ metric. In short, increased BOL $E_g$-$V_{oc}$ may be the most problematic shortcoming of aluminum containing wheel's; the other limitations can be mitigated by modifying the doping schedule or thinning base thicknesses.

Furthermore, at BOL, it is widely accepted that great subcells have a room temperature $E_g$-$V_{oc}$ of approximately 0.40. A wide variation in BOL $E_g$-$V_{oc}$ may exist for subcells of reveal that aluminum containing subcells perform no worse than other materials used in III-V solar cells. For example, all of the snivel's at EOL, regardless of aluminum concentration or degree of lattice-mismatch, have been shown to display a nearly-fixed $E_g$-$V_{oc}$ of approximately 0.6 at room temperature 28° C.

The exemplary metamorphic multijunction solar cell design philosophy may be described as opposing conventional cell efficiency improvement paths that employ infrared subcells that increase in expense as the bandgap of the materials decreases. For example, proper current matching among all subcells that span the entire solar spectrum is often a normal design goal. Further, known approaches— including dilute nitrides grown by MBE, upright metamorphic, and inverted metamorphic multi junction solar cell designs—may add significant cost to the cell and only marginally improve HT-EOL performance. Still farther, lower HT-EOL $/W may be achieved when inexpensive high bandgap subcells are incorporated into the cell architecture, rather than more expensive infrared subcells. The key to enabling the exemplary solar cell design philosophy described herein is the observation that aluminum containing subcells perform well at HT-EOL.

Figure 7A:
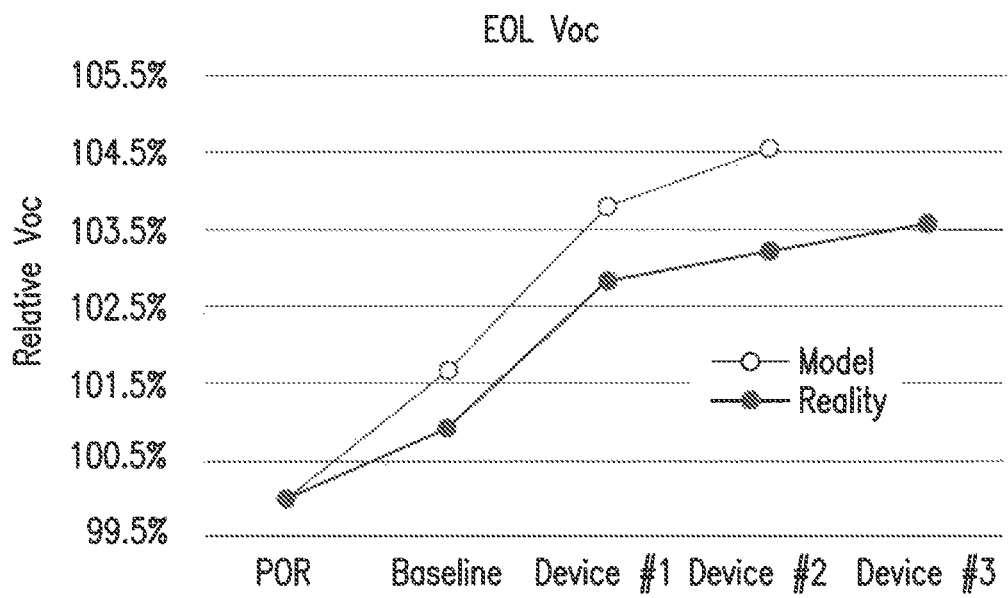
FIGS. 7A and 7B are graphs depicting the comparison of the $V_{oc}$ and FF respectively of a single junction test solar subcell comparing prior art test solar subcells with a non-graded band gap with a single junction test solar subcell with a graded band gap according to the present disclosure.

FIG. 7A is a graph depicting the relative $V_{oc}$ of three different single junction test solar cell devices with a graded band gap according to the present disclosure compared to two baseline single junction test solar cell devices which have a constant band gap, both in terms of a theoretical model and in WI ns of an experimental measurement on actual test specimens. The result, both for the model and the actual test device (indicated as the "reality" graph) demonstrates the improvement in $V_{oc}$ in the test solar cell.

Test device #1 was a 50 meV/5% AlGaAs peak in the graded region, and the graded slopes extended 100 nm from the center of the depletion region towards both the base and the emitter (again symmetric). Test device #2 and test device #3 were 100 meV/10% AlGaAs and 150 meV/15% AlGaAs subcells respectively.

Figure 7B:
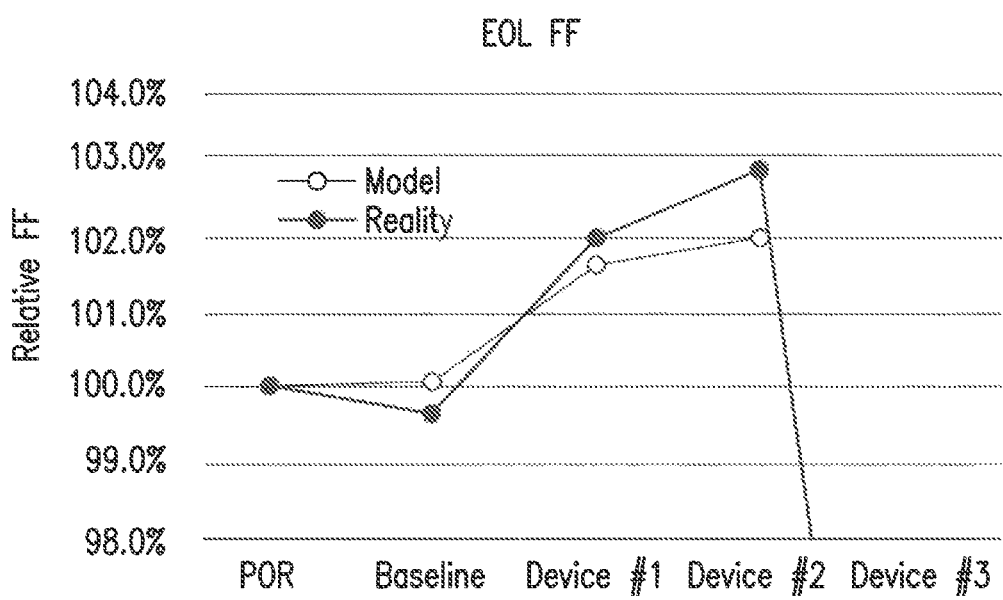

FIG. 7B is a graph depicting the relative FF of three different single junction test solar cell devices with a graded band gap according to the present disclosure compared to two baseline single junction test solar cell devices which have a constant band gap, both in terms of a theoretical model and in terms of an experimental measurement on actual test specimens. The results, both for the model and the actual test device (indicated as the "reality" graph) demonstrates the improvement in FF in the test solar subcell of device #1 and device #2 was superior over the baseline devices. The result on device #3 was substantially inferior FF.

The results on Device #3 depicted in FIG. 7B demonstrate that the design factors of variable composition and the corresponding variable band gap are not "result effective variables" since the increase in band gap to a higher level at the junction may result in a substantial sharp decrease in Fill Factor after a certain point, and therefore a substantial decrease in power. Such a composition would make such a device designed with such a band gap as inefficient and commercially impractical. The fact that the model data did not predict such a sharp drop in the FF, underscores the assertion that "band gap" in NOT a "result effective variable" in actual fabricated devices.

Combining the results of FIGS. 7A and 7B, the product of $V_{oc}$ and FF shows substantial improvement in power output of the test solar cell devices #1 and #2. Device #2 has an increase of 3.5% in $V_{oc}$ and 2% in FF, and therefore demonstrate the efficacy of employing a graded band gap in a multifunction solar cell.

Figure 8:
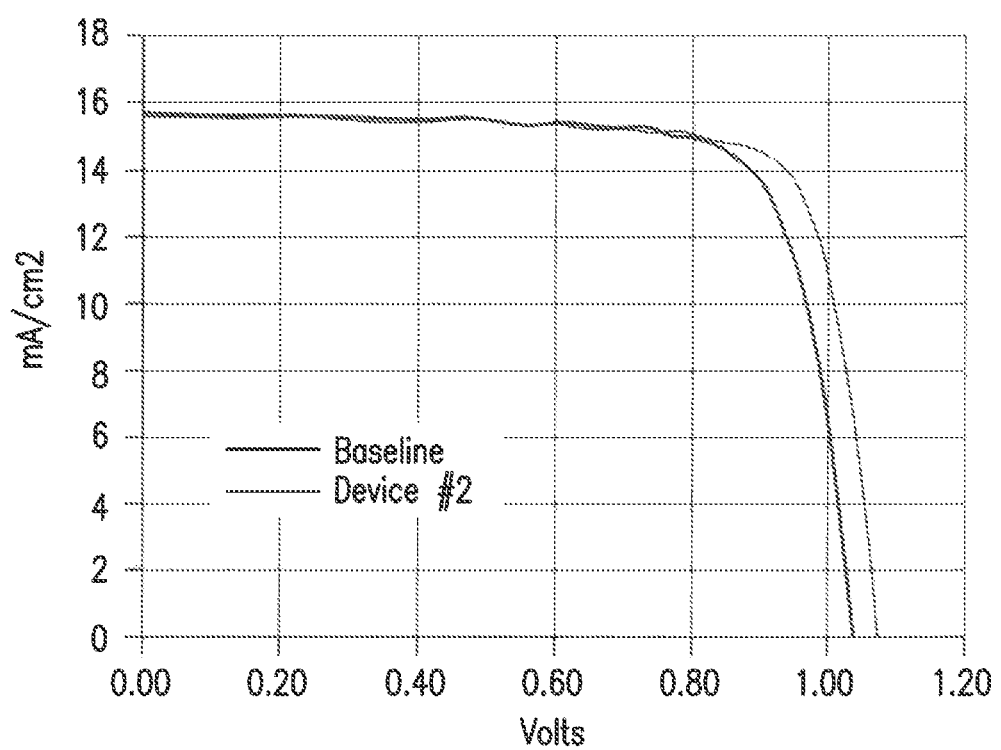
FIG. 8 is a graph depicting the current versus voltage curve of a single junction baseline test solar subcell with a single junction compared to a test solar subcell (labelled Device #2) with a graded band gap according to the present disclosure.

FIG. 8 is a graph depicting the measured current versus voltage curve of a single junction baseline test solar subcell with a single junction compared to a test solar nil/cell with a graded band gap (labelled device #2) according to the present disclosure, thereby demonstrating the improvement in power output from such subcell.

FIG. 9 is a highly simplified perspective illustration of an exemplary space vehicle including a deployable flexible sheet including an array of solar cells according to the present disclosure which may be implemented in LEO or GEO or bits, or in other space missions.

It will be understood that each of the elements described above, or two or more together, also may find a useful application in other types of structures or constructions differing from the types of structures or constructions described above.

The terminology used in this disclosure is for the purpose of describing specific identified embodiments only and is not intended to be limiting of different examples or embodiments.

In the drawings, the position, relative distance, lengths, widths, and thicknesses of supports, substrates, layers, regions, films, etc., may be exaggerated for presentation simplicity or clarity. Like reference numerals designate like elements throughout the specification. It will be understood that when an element such as an element layer, film, region, or feature is referred to as being "on" another element, it can be disposed directly on the other element or the presence of intervening elements may also be possible. In contrast, when an element is referred to as being disposed "directly on" another element, there are no intervening elements present.

Furthermore, those skilled in the art will recognize that boundaries and spacings between the above described units/operations are merely illustrative. The multiple units/operations may be combined into a single unit/operation, a single unit/operation may be distributed in additional units/operations, and units/operations may be operated at least partially overlapping in time. Moreover, alternative embodiments may include multiple instances of a particular unit/operation, and the order of operations may be altered in various other embodiments.

The terms "substantially", "essentially", "approximately", "about", or any other similar expression relating to particular parametric numerical value are defined as being close to that value as understood by one of ordinary skill in the art in the context of that parameter, and in one non-limiting embodiment the term is defined to be within 10% of that value, in another embodiment within 5% of that value, in another embodiment within 1% of that value, and in another embodiment within 0.5% of that value.

The term "coupled" as used herein is defined as connected, although not necessarily directly or physically adjoining, and not necessarily structurally or mechanically. A device or structure that is "configured" in a certain way is arranged or configured in at least that described way, but may also be arranged or configured in ways that are not described or depicted.

The terms "front", "back", "side", "top", "bottom", "over", "on", "above", "beneath", "below", "under", and the like in the description and the claims, if any, are used for descriptive purposes and not necessarily for describing permanent relative positions. It is understood that the terms so used are interchangeable under appropriate circumstances such that the embodiments of the disclosure described herein are, for example, capable of operation in other orientations than those illustrated or otherwise described herein. For example, if the assembly in the figures is inverted or turned over, elements of the assembly described as "below" or "beneath" other elements or features would then be oriented "above" the other elements or features. Thus, the exemplary term "below" can encompass both an orientation of above and below. The assembly may be otherwise oriented (rotated by a number of degrees through an axis).

The terms "front side" and "backside" refer to the final arrangement of the panel, integrated cell structure or of the individual solar cells with respect to the illumination or incoming light incidence.

In the claims, the word 'comprising' or 'having' does not exclude the presence of other elements or steps than those listed in a claim. It is understood that the terms "comprises", "comprising", "includes", and "including" if used herein, specify the presence of stated components, elements, features, steps, or operations, components, but do not preclude the presence or addition of one or more other components, elements, features, steps, or operations, or combinations and permutations thereof.

The terms "a" or "an", as used herein, are defined as one or more than one. Also, the use of introductory phrases such as "at least one" and "one or more" in the claims Should not be construed to imply that the introduction of another claim element by the indefinite articles "a" or "an" limits any particular claim containing such introduced claim element to disclosures containing only one such element, even when the claim includes the introductory phrases "one or more" or "at least one" and indefinite articles such as "a" or "an". The same holds true for the use of definite articles.

The present disclosure can be embodied in various ways. To the extent a sequence of steps are described, the above described orders of the steps for the methods are only intended to be illustrative, and the steps of the methods of the present disclosure are not limited to the above specifically described orders unless otherwise specifically stated. Note that the embodiments of the present disclosure can be freely combined with each other without departing from the spirit and scope of the disclosure.

Although some specific embodiments of the present disclosure have been demonstrated in detail with examples, it should be understood by a person skilled in the art that the above examples are only intended to be illustrative but not to limit the scope and spirit of the present disclosure. The above embodiments can be modified without departing from the scope and spirit of the present disclosure which are to be defined by the attached claims. Accordingly, other implementations are within the scope of the claims.

Although described embodiments of the present disclosure utilizes a vertical stack of a certain illustrated number of subcells, various aspects and features of the present disclosure can apply to stacks with fewer or greater number of subcells, i.e. two junction cells, three junction cells, four, five, six, seven junction cells, etc.

In addition, although the disclosed embodiments are configured with top and bottom electrical contacts, the subcells may alternatively be contacted by means of metal contacts to laterally conductive semiconductor layers between the subcells. Such arrangements may be used to form 3-terminal, 4-terminal, and is general, n-terminal devices. The subcells can be interconnected in circuits using these additional terminals such that most of the available photogenerated current density in each subcell can be used effectively, leading to high efficiency for the multijunction cell, notwithstanding that the photogenerated current densities are typically different in the various subcells.

As noted above, the solar cell described in the present disclosure may utilize an arrangement of one or more, or all, homojunction cells or subcells, i.e., a cell or subcell in which the p-n junction is formed between a p-type semiconductor and an n-type semiconductor both of which have the same chemical composition and the same band gap, differing only in the dopant species and types, and one or more heterojunction cells or subcells. Subcell C, with p-type and n-type InGaAs is one example of a homojunction subcell.

In some cells, a thin so-called "intrinsic layer" may be placed between the emitter layer and base layer, with the same or different composition from either the emitter or the base layer. The intrinsic layer may function to suppress minority-carrier recombination in the space-charge region. Similarly, either the base layer or emitter layer may also be intrinsic or not-intentionally-doped ("NID") over part or all of its thickness.

The composition of the window or BSF layers may utilize other semiconductor compounds, subject to lattice constant and band gap requirements, and may include AlInP, AlAs, AlP, AlGaInP, AlGaAsP, AlGaInAs, AlGaInPAs, GaInP, GaInAs, GaInPAs, AlGaAs, AlInAs, AlInPAs, GaAsSb, GaAsSb, AlInSb, GaInSb, AlGaInSb, AlN, GaN, InN, GaInN, AlGaInN, GaInNAs, AlGaInNAs, ZnSSe, CdSSe, and similar materials, and still fall within the spirit of the present invention.

Thus, while the description of the semiconductor device described in the present disclosure has focused primarily on solar cells or photovoltaic devices, persons skilled in the art know that other optoelectronic devices, such as thermophotovoltaic (TPV) cells, photodetectors and light-emitting diodes (LEDS), are very similar in structure, physics, and materials to photovoltaic devices with some minor variations in doping and the minority carrier lifetime. For example, photodetectors can be the same materials and structures as the photovoltaic devices described above, but perhaps more lightly-doped for sensitivity rather than power production. On the other hand, LEDs can also be made with similar structures and materials, but perhaps more heavily-doped to shorten recombination time, thus radiative lifetime to produce light instead of power. Therefore, this invention also applies to photodetectors and LEDs with structures, compositions of matter, articles of manufacture, and improvements as described above for photovoltaic cells.

Without further analysis, from the forgoing others can, by applying current knowledge, readily adapt the present invention for various applications. Such adaptions should and are intended to be comprehended within the meaning and range of equivalence of the following claims.

The invention claimed is:

1. A multijunction solar cell comprising:
    first solar subcell, having an emitter layer and a base layer which form a photoelectric junction;
    a second solar subcell disposed below and adjacent to the first solar subcell, having an emitter layer and a base layer which form a photoelectric junction; and
    a third solar subcell disposed below the second solar subcell, having an emitter layer and a base layer which form a photoelectric junction;
    wherein the base layer and the emitter layer of at least one of the first solar subcell, the second solar subcell, and the third solar subcell, has a graded band gap throughout at least a portion of the thickness of its emitter layer or its base layer in a first region in the emitter layer adjacent to the photoelectric junction, and throughout at least a portion of the thickness of its base layer in a second region spaced apart from the first region and adjacent to the photoelectric junction, with the band gap in the first region and the band gap in the second region being in the range of 20 to 300 meV greater than the band gap away from the photoelectric junction in the emitter layer or the base layer in the at least one subcell.

2. A solar cell as defined in claim 1, wherein the thickness of the first region is equal to the thickness of the second region.

3. A solar cell as defined in claim 1, wherein the band gap in the emitter layer in the first region in the at least one of the first solar subcell, the second solar subcell, and the third solar subcell increases to a first level, and then decreases to a second level in the base layer in the at least one that is lower in band gap than the first level in the emitter layer.

4. A solar cell as defined in claim 1, further comprising a third region in the emitter layer in the at least one of the first solar subcell, the second solar subcell, and the third solar subcell that lies directly adjacent to and spaced apart from the first region, wherein the band gap in the third region is constant.

5. A solar cell as defined in claim 2, further comprising a fourth region in the base layer in the at least one of the first solar subcell, the second solar subcell, and the third solar subcell that lies directly adjacent to and spaced apart from the second region, wherein the band gap in the fourth region is constant.

6. A solar cell as defined in claim 3, wherein the first level of the band gap is substantially located at the photoelectric junction of the at least one of the first solar subcell, the second solar subcell, and the third solar subcell.

7. A solar cell as defined in claim 3, wherein the second level of the band gap is substantially located in the depletion region in the base layer of the at least one of the first solar subcell, the second solar subcell, and the third solar subcell.

8. A solar cell as defined in claim 5, wherein the band gap in the third region of the at least one solar subcell equals the band gap in the fourth region of the at least one of the first solar subcell, the second solar subcell, and the third solar subcell.

9. A solar cell as defined in claim 1, wherein the depletion region of the at least one solar subcell is asymmetric around the photoelectric junction of the at least one of the first solar subcell, the second solar subcell, and the third solar subcell.

10. A solar cell as defined in claim 1, wherein the width of the graded band gap region in the at least one of the first solar subcell, the second solar subcell, and the third solar subcell is equal to the width of a depletion region in the at least one solar subcell.

11. A solar cell as defined in claim 1, wherein the band gap of the at least one of the first solar subcell, the second solar subcell, and the third solar subcell has a peak that is centered approximately where a Fermi level of the at least one solar subcell crosses mid-band.

12. A solar cell as defined in claim 1, wherein the first and second regions of the graded band gap of the at least one of the first solar subcell, the second solar subcell, and the third solar subcell is asymmetric around the depletion region of the at least solar one subcell.

13. A solar cell as defined in claim 1, wherein the first and second region of the graded band gap of the at least one of the first solar subcell, the second solar subcell, and the third solar subcell is (i) symmetric around the junction, or (ii) non-symmetric around the photoelectric junction.

14. A solar cell as defined in claim 1, and the first solar subcell is composed of indium gallium aluminum phosphide and has a first band gap in the range of 2.0 to 2.2 eV, wherein the emitter layer of the second solar subcell is composed of indium gallium phosphide or aluminum indium gallium arsenide, and the base layer is composed of aluminum indium gallium arsenide, the second solar subcell has a second band gap in the range of approximately 1.55 to 1.8 eV and being lattice matched with the first solar subcell, and wherein the third solar subcell is disposed adjacent to said second solar subcell and is composed of indium gallium arsenide and has a third band gap less than the second band gap of the second solar subcell and is lattice matched with the second solar subcell.

15. A solar cell as defined in claim 14, wherein the solar cell is configured for optimum operation in (i) a LEO earth orbit; (ii) a GEO earth orbit; (iii) a Mars environment; or (iv) a Jupiter environment.

16. A solar cell as defined in claim 1, wherein the first solar subcell, the second solar subcell, and the third solar subcell each have a graded band gap throughout at least a portion of the thickness of their emitter layer and base layer.

17. A solar cell as defined in claim 1, further comprising an intermediate graded layer disposed between one of the first solar subcell, the second solar subcell, and the third solar subcell and the adjacent solar subcell disposed directly below the one solar subcell, wherein the intermediate layer is compositionally graded to lattice match the one solar subcell on one side and the adjacent solar subcell on the other side and is composed of any of the As, P, N, Sb based III-V compound semiconductors subject to the constraints of having the in-plane lattice parameter greater than or equal to that of the one solar subcell and less than or equal to that of the adjacent solar subcell, and having a band gap greater than that of the one solar subcell.

18. A solar cell as defined in claim 1, further comprising a bottom solar subcell disposed below the third solar subcell, and an intermediate graded layer disposed between the third solar subcell and the bottom solar subcell, wherein the intermediate layer is compositionally step-graded with between one and four steps to lattice match the third solar subcell on one side and the bottom solar subcell on the other side and composed of InGaAs or $(In_xGa_{1-x})_yAl_{1-y}As$ with $0<x<1$, $0<y<1$, and x and y selected such that the band gap remains at a constant value in the range of 1.15 to 1.41 eV, or 1.2 to 1.35 eV, or 1.25 to 1.30 eV throughout its thickness.

19. A solar cell as defined in claim 14, further comprising:
a distributed Bragg reflector (DBR) layer disposed adjacent to and beneath the third solar subcell and arranged so that light can enter and pass through the third solar subcell and at least a portion of which can be reflected back into the third solar subcell by the DBR layer, wherein the distributed Bragg reflector layer is composed of a plurality of alternating layers of lattice matched materials with discontinuities in their respective indices of refraction, wherein the difference in refractive indices between alternating layers is maximized in order to minimize the number of periods required to achieve a given reflectivity, and the thickness and refractive index of each period determines the stop band and its limiting wavelength, and wherein the DBR layer includes a first DBR layer composed of a plurality of p-type $Al_xGa_{1-x}As$ layers, and a second DBR layer disposed over the first DBR layer and composed of a plurality of p-type $Al_yGa_{1-y}As$ layers, where $0<x<1$, $0<y<1$, and y is greater than x; and an intermediate layer disposed between the DBR layer and the growth substrate, wherein the intermediate layer is compositionally step-graded to lattice match the DBR layer on one side and the growth substrate on the other side, and is composed of any of the As, P, N, Sb based III-V compound semiconductors subject to the constraints of having the in-plane lattice parameter greater than or equal to that of the DBR layer and less than or equal to that of the growth substrate.

* * * * *